United States Patent
Kim et al.

(10) Patent No.: US 11,859,207 B2
(45) Date of Patent: Jan. 2, 2024

(54) ARTIFICIAL ANTIGEN-PRESENTING CELL PREPARED FROM HLA-NULL CELL LINE BY USING MULTIPLEX CRISPR-CAS9 SYSTEM AND USE THEREOF

(71) Applicant: THE CATHOLIC UNIVERSITY OF KOREA INDUSTRY-ACADEMIC COOPERATION FOUNDATION, Seoul (KR)

(72) Inventors: Tai Gyu Kim, Seoul (KR); Hyun Jung Sohn, Seoul (KR); Cheol Hwa Hong, Seoul (KR)

(73) Assignee: The Catholic Uiversity of Korea Industry-Academic Cooperation Foundation, Seoul (KR)

( * ) Notice: Subject to any disclaimer, the term of this patent is extended or adjusted under 35 U.S.C. 154(b) by 1077 days.

(21) Appl. No.: 16/465,933

(22) PCT Filed: Dec. 1, 2017

(86) PCT No.: PCT/KR2017/014027
§ 371 (c)(1),
(2) Date: May 31, 2019

(87) PCT Pub. No.: WO2018/101796
PCT Pub. Date: Jun. 7, 2018

(65) Prior Publication Data
US 2019/0309260 A1    Oct. 10, 2019

(30) Foreign Application Priority Data
Dec. 2, 2016  (KR) .................. 10-2016-0163509

(51) Int. Cl.
| | |
|---|---|
| *C12N 5/078* | (2010.01) |
| *A61K 35/17* | (2015.01) |
| *C07K 14/74* | (2006.01) |
| *C12N 5/0783* | (2010.01) |
| *C12N 9/22* | (2006.01) |
| *C12N 15/11* | (2006.01) |
| *C12N 15/85* | (2006.01) |
| *C12N 15/63* | (2006.01) |

(52) U.S. Cl.
CPC ............ *C12N 5/0634* (2013.01); *A61K 35/17* (2013.01); *C07K 14/70539* (2013.01); *C12N 5/0638* (2013.01); *C12N 9/22* (2013.01); *C12N 15/11* (2013.01); *C12N 15/63* (2013.01); *C12N 15/85* (2013.01); *C12N 2310/20* (2017.05); *C12N 2502/99* (2013.01); *C12N 2800/80* (2013.01)

(58) Field of Classification Search
CPC .......... C07K 14/70539; C12N 15/1138; C12N 15/63; C12N 2310/20; C12N 2502/99; C12N 15/85; C12N 5/0638; C12N 9/22; C12N 15/11; C12N 2800/80; C12N 2510/00; C12N 5/0634; A61K 35/17
See application file for complete search history.

(56) References Cited

U.S. PATENT DOCUMENTS

| | | | |
|---|---|---|---|
| 8,124,408 B2 * | 2/2012 | Cai ................ | A61K 39/001182 435/348 |
| 10,968,426 B2 * | 4/2021 | Meissner ............. | C12N 5/0696 |
| 2006/0034810 A1 | 2/2006 | Riley et al. | |

FOREIGN PATENT DOCUMENTS

| | | | | |
|---|---|---|---|---|
| WO | WO 2014165825 A2 * | 4/2013 | ............. | A61P 31/18 |
| WO | 2016-183041 A2 | 11/2016 | | |

OTHER PUBLICATIONS

Butler et al., Establishing CD8+ T Cell Immunity by Adoptive Transfer of Autologous, IL-15 Expanded, Anti-Tumor CTL with a Central/Effector Memory Phenotype Can Induce Objective Clinical Responses. Blood (2009) 114 (22) : 782. (Year: 2009).*
Durai et al, In vivo functional eYcacy of tumor-speciWc T cells expanded using HLA-Ig based artiWcial antigen presenting cells (aAPC). Cancer Immunol Immunother (2009) 58: 209-220. (Year: 2009).*
Wikimedia Foundation. (May 19, 2022). HEK 293 cells. Wikipedia. Retrieved Jul. 14, 2022, from https://en.wikipedia.org/wiki/HEK_293_cells#:~:text=293T%20(or%20HEK%20293T)%20is,proteins%20and%20producing%20recombinant%20retroviruses. (Year: 2013).*
Oelke et al, Ex vivo induction and expansion of antigen-specific cytotoxic T cells by HLA-Ig-coated artificial antigen-presenting cells. Nat Med (2003) 9: 619-625. (Year: 2003).*
Williams, Human Leukocyte Antigen Gene Polymorphism and the Histocompatibility Laboratory. J Mol Diagn. (2001) 3(3): 98-104. (Year: 2001).*
Latouche et al. Induction of human cytotoxic T lymphocytes by artificial antigen-presenting cells. Nat Biotechnol 18, 405-409 (2000). https://doi.org/10.1038/74455 (Year: 2000).*

(Continued)

*Primary Examiner* — Allison M Fox
*Assistant Examiner* — Alyssa G Weston
(74) *Attorney, Agent, or Firm* — Meunier Carlin & Curfman LLC

(57) ABSTRACT

The present invention relates to an artificial antigen-presenting cell prepared from an HLA-null cell line by using a multiplex CRISPR-Cas9 system and the use thereof and, more particularly, to a novel artificial antigen-presenting cell which includes the ability to present antigens of HLA class I and a co-stimulatory molecule group transferred from an HLA-A, -B, -C null cell line generated using a multiplex CRISPR-Cas9 system and to stimulate T cells, an immunotherapeutic agent using the same, and the use thereof for treating tumors, pathogenic infections, and autoimmune diseases.

1 Claim, 13 Drawing Sheets
Specification includes a Sequence Listing.

(56) References Cited

OTHER PUBLICATIONS

Zhang et al. The significance of controlled conditions in lentiviral vector titration and in the use of multiplicity of infection (MOI) for predicting gene transfer events. Genet Vaccines Ther. Aug. 4, 2004;2(1):6. doi: 10.1186/1479-0556-2-6. (Year: 2004).*

International Search Report issued by the International Searching Authority (KR) in PCT Application No. PCT/KR2017/014027 dated Mar. 26, 2018, 5 pages.

Butler, Marcus O., et al. "Long-lived antitumor CD8+ lymphocytes for adoptive therapy generated using an artificial antigen-presenting cell." Clinical Cancer Research 13.6 (2007): 1857-1867.

Hong, Cheol-Hwa, et al. "Antigen presentation by individually transferred HLA class I genes in HLA-A, HLA-B, HLA-C null human cell line generated using the multiplex CRISPR-cas9 system." Journal of Immunotherapy 40.6 (2017): 201-210.

Suhoski, Megan M., et al. "Engineering artificial antigen-presenting cells to express a diverse array of co-stimulatory molecules." Molecular Therapy 15.5 (2007): 981-988.

Torikai, Hiroki, et al. "Toward eliminating HLA class I expression to generate universal cells from allogeneic donors." Blood 122.8 (2013): 1341-1349.

Zeng, Wanyong, et al. "Artificial antigen-presenting cells expressing CD80, CD70, and 4-1BB ligand efficiently expand functional T cells specific to tumor-associated antigens." Immunobiology 219.8 (2014): 583-592.

Latouche et al. Induction of human cytotoxic T lymphocytes by artificial antigen-presenting cells; Nat. Biotechnology 18; 405-409; Feb. 2, 2000.

Zhang et al. The significance of controlled conditions in lentiviral vector titration and in the use of multiplicity of infection (MOI) for predicting gene transfer events; Genetic Vaccines & Therapy 2:6; Aug. 4, 2004.

* cited by examiner

SEQUENCE LISTING

```
<160> NUMBER OF SEQ ID NOS: 16

<210> SEQ ID NO 1
<211> LENGTH: 23
<212> TYPE: DNA
<213> ORGANISM: Artificial Sequence
<220> FEATURE:
<223> OTHER INFORMATION: HLA-A exon 2 target sequence

<400> SEQUENCE: 1
gagccagagg atggagccgc ggg                                           23

<210> SEQ ID NO 2
<211> LENGTH: 23
<212> TYPE: DNA
<213> ORGANISM: Artificial Sequence
<220> FEATURE:
<223> OTHER INFORMATION: HLA-A exon 3 target sequence

<400> SEQUENCE: 2
gaaggagacg ctgcagcgca cgg                                           23

<210> SEQ ID NO 3
<211> LENGTH: 23
<212> TYPE: DNA
<213> ORGANISM: Artificial Sequence
<220> FEATURE:
<223> OTHER INFORMATION: HLA-B exon 2 target sequence

<400> SEQUENCE: 3
```

```
gctgtcgaac ctcacgaact ggg                                              23

<210> SEQ ID NO 4
<211> LENGTH: 23
<212> TYPE: DNA
<213> ORGANISM: Artificial Sequence
<220> FEATURE:
<223> OTHER INFORMATION: HLA-B exon 3 target sequence

<400> SEQUENCE: 4
gagcatgtac ggctgcgacg tgg                                              23

<210> SEQ ID NO 5
<211> LENGTH: 23
<212> TYPE: DNA
<213> ORGANISM: Artificial Sequence
<220> FEATURE:
<223> OTHER INFORMATION: HLA-C exon 2 target sequence

<400> SEQUENCE: 5
gacacagaag tacaagcgcc agg                                              23

<210> SEQ ID NO 6
<211> LENGTH: 23
<212> TYPE: DNA
<213> ORGANISM: Artificial Sequence
<220> FEATURE:
<223> OTHER INFORMATION: HLA-C exon 3 target sequence

<400> SEQUENCE: 6
ccagaggatg tctggctgcg acc                                              23

<210> SEQ ID NO 7
<211> LENGTH: 10
<212> TYPE: PRT
<213> ORGANISM: Artificial Sequence
<220> FEATURE:
<223> OTHER INFORMATION: MART-1 26-35

<400> SEQUENCE: 7

Glu Leu Ala Gly Ile Gly Ile Leu Thr Val
1               5                   10

<210> SEQ ID NO 8
<211> LENGTH: 9
<212> TYPE: PRT
<213> ORGANISM: Artificial Sequence
<220> FEATURE:
<223> OTHER INFORMATION: pp65 495-503

<400> SEQUENCE: 8

Asn Leu Val Pro Met Val Ala Thr Val
1               5

<210> SEQ ID NO 9
<211> LENGTH: 8
<212> TYPE: PRT
<213> ORGANISM: Artificial Sequence
<220> FEATURE:
<223> OTHER INFORMATION: Ova257

<400> SEQUENCE: 9

Ser Ile Ile Asn Phe Glu Lys Leu
1               5

<210> SEQ ID NO 10
```

```
<211> LENGTH: 9
<212> TYPE: PRT
<213> ORGANISM: Artificial Sequence
<220> FEATURE:
<223> OTHER INFORMATION: tyrosinase-related protein 1455 (Trp1455)

<400> SEQUENCE: 10

Thr Ala Pro Asp Asn Leu Gly Tyr Ala
1               5

<210> SEQ ID NO 11
<211> LENGTH: 9
<212> TYPE: PRT
<213> ORGANISM: Artificial Sequence
<220> FEATURE:
<223> OTHER INFORMATION: Trp2 180

<400> SEQUENCE: 11

Ser Val Tyr Asp Phe Phe Val Trp Leu
1               5

<210> SEQ ID NO 12
<211> LENGTH: 9
<212> TYPE: PRT
<213> ORGANISM: Artificial Sequence
<220> FEATURE:
<223> OTHER INFORMATION: gp100 25

<400> SEQUENCE: 12

Glu Gly Ser Arg Asn Gln Asp Trp Leu
1               5

<210> SEQ ID NO 13
<211> LENGTH: 9
<212> TYPE: PRT
<213> ORGANISM: Artificial Sequence
<220> FEATURE:
<223> OTHER INFORMATION: MAGE 1 nonapeptide

<400> SEQUENCE: 13

Glu Ala Asp Pro Thr Gly His Ser Tyr
1               5

<210> SEQ ID NO 14
<211> LENGTH: 9
<212> TYPE: PRT
<213> ORGANISM: Artificial Sequence
<220> FEATURE:
<223> OTHER INFORMATION: MART-APL peptide

<400> SEQUENCE: 14

Leu Ala Gly Ile Gly Ile Leu Thr Val
1               5

<210> SEQ ID NO 15
<211> LENGTH: 9
<212> TYPE: PRT
<213> ORGANISM: Artificial Sequence
<220> FEATURE:
<223> OTHER INFORMATION: natural peptide

<400> SEQUENCE: 15

Ala Ala Gly Ile Gly Ile Leu Thr Val
1               5

<210> SEQ ID NO 16
<211> LENGTH: 10
```

```
<212> TYPE: PRT
<213> ORGANISM: Artificial Sequence
<220> FEATURE:
<223> OTHER INFORMATION: PSA-1 peptide

<400> SEQUENCE: 16

Phe Leu Thr Pro Lys Lys Leu Gln Cys Val
1               5                   10
```

ARTIFICIAL ANTIGEN-PRESENTING CELL PREPARED FROM HLA-NULL CELL LINE BY USING MULTIPLEX CRISPR-CAS9 SYSTEM AND USE THEREOF

BACKGROUND

1. Field of the Invention

The present invention relates to a novel artificial antigen-presenting cell which includes antigen-presenting and T cells-stimulating abilities of HLA class I molecules and a co-stimulatory molecule group transferred from an HLA-A, -B, -C null cell line generated by using a multiplex CRISPR-Cas9 system, and the use thereof.

2. Discussion of Related Art

As the major histocompatibility complex (MHC) of humans, the human leukocyte antigen (HLA) molecules are most important immunological molecules in humans. It consist of two major sets, the HLA class I (HLA-A, -B, -C) and HLA class II (HLA-DR, -DP, -DQ), which present antigens to CD8+T cells and CD4+T cells, respectively. A high level of polymorphism has been demonstrated in HLA molecules, and this makes it possible to present unique peptides or may provoke alloreactive immune responses. Further, mismatches of HLA alleles are able to induce graft rejection in organ transplantation or graft versus host disease (GVHD) in hematopoietic stem cell transplantation (HSCT).

To overcome many limitations in transplantation and cell therapy, many studies have been performed for regulating HLA expression. The HLA regulation has been studied using the leukemia cell lines and lymphoblastoid cell lines (LCLs) with γ-ray induced mutations and somatic cell hybridizations. These HLA null cell lines have been used for definitive studies about the structure and function of specific HLA molecules and as a source of artificial antigen presenting cells (AAPCs) for efficient adoptive cell therapy. Particularly, AAPCs have been developed from *Drosophila*, mouse and human leukemia cell lines by gene transfer of HLA and co-stimulatory molecules.

As genetic regulation tools develop, many studies about the HLA regulation have been reported for universal applications. Short hairpin RNAs (shRNAs) were used for down regulation of HLA expression in various cells such as Jurkat, T cells, HeLa, B-LCL, 293T cells, hematopoietic stem cells, human embryonic stem cell (hESC) lines, and human cord blood derived endothelial cells. These reports demonstrated the effects of HLA silencing by targeting specific HLA alleles or beta-2-microglobulin (B2M) which is a heterodimer of HLA class 1 molecules. Also, they proposed respective applications such as circumvention of allograft rejection, cell therapy, and management of platelet transfusion. The loxP/Cre system was also used in B2M knockout for HLA negative embryonic stem cell lines.

Recently, the possibility of HLA regulation was demonstrated with gene editing tools such as zinc finger nucleases (ZFNs) and a CRISPR-associated protein 9 (Cas9) system. In particular, the CRISPR-Cas9 system is a technology well-suited for multiplexed gene editing. In addition, the CRISPR-Cas9 system is able to induce large deletions mediated by multiple guide RNAs (gRNAs). The ZFN was used to eliminate the HLA-A gene. Also, the CRISPR/Cas9 system was used to eliminate the B2M gene, and for the regulation of HLA class II expression, class II transactivator (CIITA) was deleted.

In the present invention, it was demonstrated that HLA class I genes were completely eliminated in human embryonic kidney (HEK) 293T cells by inducing large deletions between exon 2 and 3 loci of HLA class I genes with a CRISPR-Cas9 system, and this HLA class I null-293 T cell line can be used as an artificial antigen presenting cell by transferring a single HLA gene and genes of a co-stimulatory molecule group, thereby completing the present invention.

SUMMARY OF THE INVENTION

An object of the present invention is to establish an HLA null cell line using a multiplex CRISPR-Cas9 system and use it as an artificial antigen presenting cell by introducing an HLA gene and a co-stimulatory molecule group.

Another object of the present invention is to provide a use of the artificial antigen presenting cell for preventing or treating tumors, pathogenic infections, and autoimmune diseases.

To achieve the objects, the present invention provides an artificial antigen presenting cell which expresses one or more HLA molecules selected from the group consisting of human leukocyte antigen (HLA)-A, -B, and -C; and a co-stimulatory molecule group including CD80, CD83, CD54, CD32, 4-1BBL, and CD70, and is derived from a human leukocyte antigen (HLA) null 293T cell line.

The present invention also provides an immunotherapeutic agent including the artificial antigen presenting cell sensitized to one or more antigens selected from the group consisting of a tumor antigen, a pathogenic antigen, and an auto-antibody.

The present invention also provides a vaccine for preventing tumors, pathogenic infections, or autoimmune diseases, including the artificial antigen presenting cell sensitized to one or more antigens selected from the group consisting of a tumor antigen, a pathogenic antigen, and an auto-antibody.

The present invention also provides a composition for treating tumors, pathogenic infections, or autoimmune diseases, including the artificial antigen presenting cell sensitized to one or more antigens selected from the group consisting of a tumor antigen, a pathogenic antigen, and an auto-antibody.

The present invention also provides a method for treating tumors, pathogenic infections, or autoimmune diseases, including a step of administering a pharmaceutical composition containing the artificial antigen presenting cell sensitized to one or more antigens selected from the group consisting of a tumor antigen, a pathogenic antigen, and an auto-antibody to a subject in need thereof.

The present invention also provides a method for in vitro proliferating cytotoxic T cells, including a step of co-culturing the artificial antigen presenting cell sensitized to one or more antigens selected from the group consisting of a tumor antigen, a pathogenic antigen, and an auto-antibody with any one T cell of a CD4+T cell, a CD8+T cell, or a γδT cell.

The present invention has effects of establishing an HLA class I null cell line by using a CRISPR-Cas9 system in a human cell line to completely eliminate HLA-A, -B, -C genes in genomes and providing an artificial antigen presenting cell having antigen-presenting and T cells-stimulating abilities by expressing a specific HLA and various co-stimulatory molecules.

BRIEF DESCRIPTION OF THE DRAWINGS

FIG. 2a is an analysis result of a genotype of each clone using target specific PCR and gel electrophoresis (the solid line arrow is a PCR product of a wild type 293T control, the dotted line arrow is a PCR product of predicted deletion between exon 2 and 3 by designed gRNAs), and FIG. 2b is a mutation distribution of each HLA class I gene region in total clones (full length: similar to wild-type 293T product size; deletion: shorter than wild-type 293T product size; insertion: longer than wild-type 293T product size; and unamplified: no band or multiple non-specific bands. The data is converted into a percentage according to a locus of an HLA class I allele).

FIG. 3a is a result of classifying the number of single cell clones according to genotypes and loci of DCP, FIG. 3b is a correlation between genotype and expression level of HLA class I in the individual clones (selected only homozygous clones and classified the groups according to the number of DCP of HLA class I alleles. The significance between the wild-type group and each mutation group through the t-test, ***: p<0.0001), and FIG. 3c is a Sanger sequencing result of selected HLA class I null clones (clones 25, 41, and 45) (N: target gRNA sequence, inverted triangles: cut site, dot: removed sequence).

FIG. 4a is a flow cytometry result that analyzes the HLA class I molecule expression in null-293 T (H1E-45) cell lines into which four types of HLA class I molecules (HLA-A*02:01, A*02:06, B*07:02, and B*40:06) are introduced and wild-type 293T cells, and FIG. 4b is an immune response result of individual HLA matched healthy donors for the CMV pp65 whole antigen (n=8).

FIG. 5a is a flow cytometry result that analyzes the expression of HLA-A*02:01, CD32 and co-stimulatory molecules (CD80, CD83, CD137L, CD54, and CD70) in an A*02:01-293T(H1E-45)-Cos cell line, FIG. 5b is the IFN-γ spot number (without peptide stimulation) per $5 \times 10^4$ individual MART-1 specific cytotoxic T cells on days 0, 13, and 19, and FIG. 5c is a picture of an ELISPOT plate without peptide (w/o) or with peptide (w/p) wells with respect to $5 \times 10^4$ individual MART-1 specific cytotoxic T cells on days 0, 13, and 19.

DETAILED DESCRIPTION OF EXEMPLARY EMBODIMENTS

Figure 1:
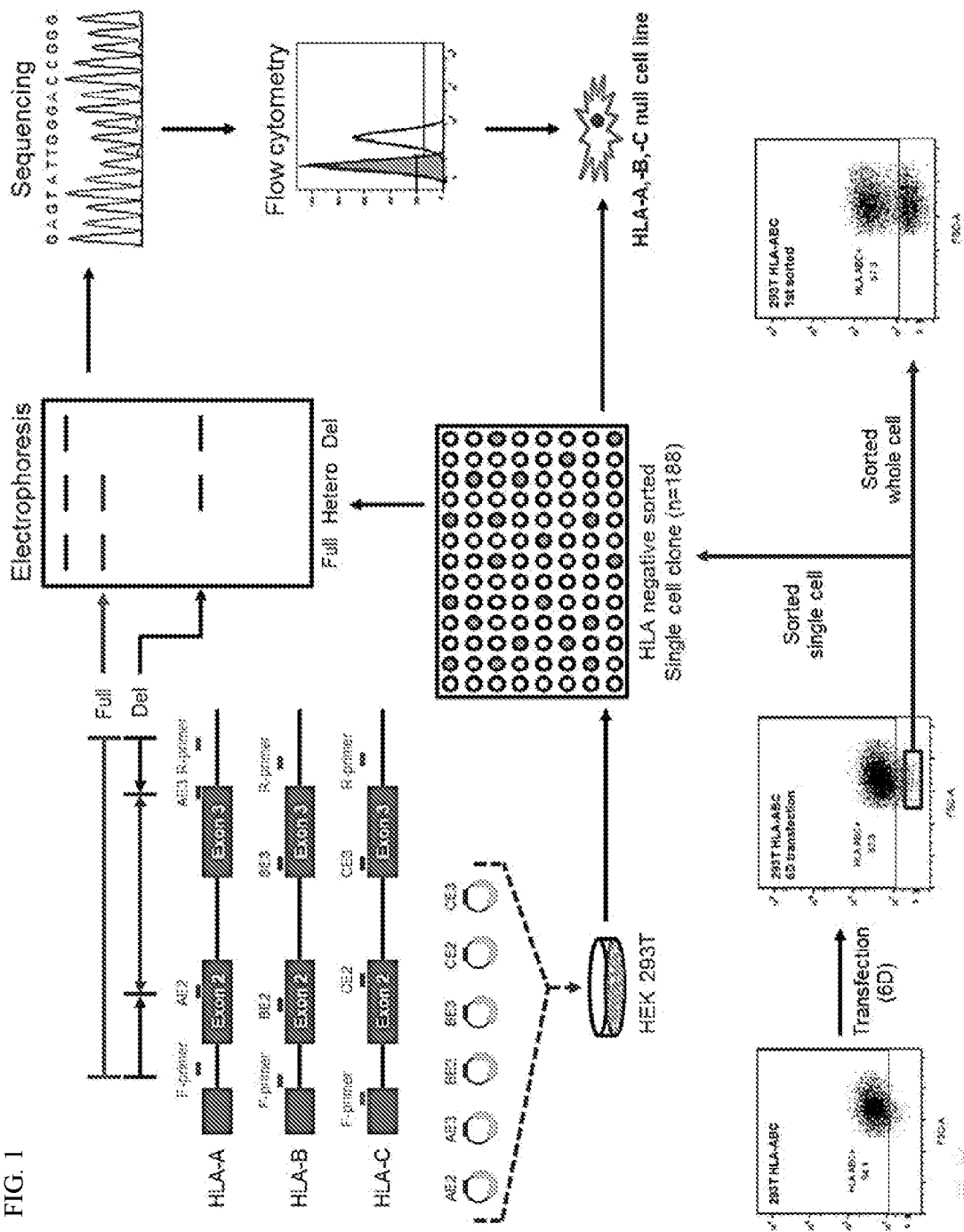
FIG. 1 illustrates a schematic summary of the establishment of HLA class I null HEK 293 cell line using a multiplex CRISPR-Cas9 system.

Hereinafter, the configuration of the present invention will be described in detail.

The present invention relates to an artificial antigen presenting cell which expresses one or more HLA molecules selected from the group consisting of human leukocyte antigen (HLA)-A, -B, and -C; and a co-stimulatory molecule group including CD80, CD83, CD54, CD32, 4-1BBL, and CD70 and is derived from a human leukocyte antigen null 293T cell line.

The present invention is characterized by providing an artificial antigen presenting cell expressing an HLA molecule and a co-stimulatory molecule group constructed so as to induce an antigen-specific cytotoxic T cell response while performing the functions of autologous antigen presenting cells as an alternative to address the disadvantages in that conventional antigen presenting cells, for example, dendritic cells, are present in small amounts in human peripheral blood mononuclear cells and it is difficult to obtain a large amount of cells for clinical application.

As used herein, the term "artificial antigen presenting cells (aAPCs)" refers to antigen presenting cells artificially constructed, and the cells are non-immune cells modified so as to express immune molecules. The aAPC which expresses MHC Class I or II (MHC I or II) either alone or together with other accessory molecules (co-stimulatory molecules and/or adhesion molecules) is used to study various aspects of T cell activated cells which may be easily cultured in vivo, such as tumor cells or fibroblast cell lines. For the purpose of the present invention, the term "artificial antigen presenting cells (aAPCs)" refers to cells in which nucleic acids encoding an HLA molecule and a co-stimulatory molecule group are introduced into cells. Preferably, the term "artificial antigen presenting cells" refers to cells in which nucleic acids encoding an HLA molecule; and a co-stimulatory molecule group including CD80, CD83, CD54, CD32, 4-1BBL, and CD70 are introduced into an HLA null 293 T cell line in which the HLA-A, -B, or -C gene is eliminated in a genome using the CRISPR-Cas9 system, but is not limited thereto.

The term "co-stimulatory molecule" refers to a substance participating in the interaction between receptor-ligand pairs and T cells, which are expressed on the surface of antigen presenting cells, and in order to induce the expression and proliferation of cytokine genes, two or more signals are required for resting T cells, the first signal is a signal imparting specificity and is produced by the interaction between an MHC/peptide complex and a TCR/CD3 complex, and the second signal is non-specific to antigen and refers to a "co-stimulatory" signal. This signal is known as an activity provided by bone-marrow-derived accessory cells such as macrophages and dendritic cells. The co-stimulatory molecule mediates a co-stimulatory signal required under normal physiological conditions to perform a complete activation of CD8+T cells. In the present invention, a combination of CD80, CD83, CD54, CD32, 4-1BBL, and CD70 is used as the co-stimulatory molecule.

The artificial antigen presenting cell may be prepared by establishing an HLA null 293T cell line in which an HLA gene is completely eliminated in a genome by deletion between exon 2 and 3 loci of each of HLA-A, -B, and -C through the CRISPR-Cas9 system, and inserting nucleic acids encoding an HLA molecule and a co-stimulatory molecule group to be introduced into the cell line.

The aforementioned RNA gene editors (RNA-guided clustered regularly interspaced short palindrome repeats (CRISPR))-associated nuclease Cas9 provides an innovative technology for suppression using a targeted knock-out, transcriptional activation, and a single guide RNA (sgRNA) (that is, a crRNA-tracrRNA fusion transcript), and the technology targets numerous loci.

For the establishment of the HLA null 293T cell line, a plasmid expressing an sgRNA including target sequences of exons 2 and 3 of an HLA-A, -B, or -C gene; and a plasmid expressing a Cas9 protein may be transfected into 293T cells, a target gene may be recognized by the sgRNA including the target sequences, a complex with the Cas9 protein may be formed, and it is possible to delete between exons 2 and 3 of the HLA-A, -B, or -C through the cleavage of the target DNA.

According to an embodiment of the present invention, in order to induce a large deletion between exon 2 and 3 of each HLA class I allele, six gRNA-Cas 9 plasmids (AE2, AE3, BE2, BE3, CE2, and CE3) are co-transfected into wild-type 293T cells, and 6D post-transfection, HLA class I negative cells are sorted and seeded as a single cell on 96-well plates by using a Moflo FACS sorter with an HLA class I monoclonal antibody. 2 to 3 weeks post-single cell seeding, single cell clones are established and cultured (n=188). For analysis of genotypes, PCR using each of specific forward (F–) and reverse (R–) primers and gel electrophoresis are carried out. Also, Sanger sequencing for analysis of a genomic sequence is carried out on selected clones. An HLA class I null cell line may be established by confirming HLA class I expression using flow cytometry with an HLA class I monoclonal antibody.

As used herein, the term "cleavage" refers to a breakage of a covalent backbone of a nucleotide molecule.

The guide RNA (sgRNA) is an RNA which contains a target sequence of an HLA-A, -B, or -C gene, and thus may be expressed through transcription after being transferred to cells to recognize the HLA-A, -B, or -C gene and form a complex with a Cas9 protein, and brings the Cas9 protein into the HLA-A, -B, or -C gene. Accordingly, the guide RNA includes a guide RNA scaffold consisting of a target sequence of an HLA-A, -B, or -C gene; and a non-variable sequence which is not relevant to the target.

The target sequence of the HLA-A, -B, or -C gene refers to a sequence that enables a guide RNA to recognize a target gene, and a suitable modification may be applied according to the type of a host cell, the type of the target gene, or the insertion site.

The guide RNA scaffold may consist of two RNAs, that is, a CRISPR RNA (crRNA) and a transactivating crRNA (tracrRNA), or may be a single-chain guide RNA (sgRNA) produced by fusion of the essential portions of the crRNA and the tracrRNA. The guide RNA may be a dual RNA including the crRNA and the tracrRNA. If the guide RNA scaffold includes essential portions of a crRNA and a tracrRNA and a portion complementary to a target, any guide RNA scaffold may be used in the present invention. The crRNA may be hybridized with a target DNA.

Preferably, the crRNA may be a single-chain guide RNA.

The terminator is linked to a DNA terminal encoding a guide RNA in order to terminate the transcription of a DNA encoding a guide RNA, may be adopted and used at a suitable selection level of those skilled in the art according to a promoter, and thus is not particularly limited, and may be, for example, an RNA polymerase III terminator or a -TTTTTT- sequence.

The Cas9 protein refers to an essential protein element in the CRISPR-Cas9 system, and forms an active endonuclease when forming a complex with two RNAs called a CRISPR RNA (crRNA) and a transactivating crRNA (tracrRNA). The information on the Cas9 gene and protein may be obtained from the GenBank of the National Center for Biotechnology Information (NCBI), but is not limited thereto.

When the Cas9 protein is transferred to cells, the Cas9 protein may be linked to a protein transduction domain. The protein transduction domain may be a poly-arginine domain or a TAT protein derived from HIV, but is not limited thereto.

The Cas9 protein may be transferred through transfection in the form of a vector expressing the Cas9 protein, that is, a vector including a nucleic acid encoding the Cas9 protein. The nucleic acid encoding the Cas9 protein may be in the form of a vector such as a plasmid including a Cas9 coding sequence downstream of a promoter such as CMV or CAG.

A plasmid expressing the sgRNA and a plasmid expressing the Cas9 protein may be transferred to cells by various methods in the art, such as microinjection, electroporation, DEAE-dextran treatment, lipofection, nanoparticle-mediated transfection, protein delivery domain-mediated introduction, protein transduction domain-mediated introduction, virus-mediated gene delivery, and PEG-mediated transfection in protozoa, but the method is not limited thereto.

The HLA null 293T cell lines established above may be used as a source of artificial antigen presenting cells capable of stimulating T cells by using a known transformation technique.

Accordingly, the artificial antigen presenting cell of the present invention may be prepared by introducing an HLA molecule; and a co-stimulatory molecule to be expressed in an HLA null 293T cell line. Preferably, nucleic acids encoding an HLA molecule and a co-stimulatory molecule group, CD80, CD83, CD54, CD32, 4-1BBL, and CD70 may be introduced.

The nucleic acids encoding the HLA molecule and the co-stimulatory molecule are used in the broadest sense, and encompass single-stranded (ss) DNA, a double-stranded (ds) DNA, cDNA, (–)-RNA, (+)-RNA, dsRNA, and the like. Preferably, the nucleic acid is double-stranded DNA.

Preferably, the HLA may be a human-derived nucleic acid sequence.

The CD80, CD83, CD54, CD32, 4-1BBL, and CD70 may be a human- or mouse-derived nucleic acid sequence, but are not limited thereto.

When a DNA is selected as the nucleic acid encoding the HLA molecule or the co-stimulatory molecule, the DNA may be used in a form in which the DNA is inserted into an expression vector.

As used herein, the term "vector" refers to a nucleic acid molecule capable of transporting another nucleic acid linked thereto. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (for example, bacterial vectors having a bacterial origin of replication and episomal mammalian vectors). Other vectors (for example, non-episomal mammalian vectors) are integrated into the genome of a host cell upon introduction into the host cell, and thereby may be replicated along with the host genome. Moreover, certain vectors are capable of directing the expression of genes to which they are operably linked. As used herein, the vector refers to a vectors useful in recombinant DNA techniques are predominantly in the form of plasmids, and "plasmid" and "vector" may be used interchangeably as the plasmid is a type of vector most commonly used. However, the present invention also includes other types of expression vectors such as viral vectors providing an equivalent function (for example, an adenoviral vector, an adeno-associated viral (AAV) vector, a herpes viral vector, a retroviral vector, a lentiviral vector, and a baculoviral vector). Preferably, a lentiviral vector may be used. Transformation includes any method of introducing nucleic acids into organisms, cells, tissues or organs and may be performed by selecting the suitable above-described standard technique depending on the type of host cell as known in the art.

As used herein, "to sensitize an artificial antigen presenting cell with a substance" refers to reacting the artificial antigen presenting cell with the substance, and preferably refers to directly or indirectly presenting the substance on the surface of the artificial antigen presenting cell. As used herein, the substance refers to an antigen, and the "foreign antigen" is an antigen which the cell itself does not possess, and may be sensitized by transferring the antigen to or contacting the antigen with cells. For the transfer, it is possible to use electroporation, transfection, and the like by pulse energy without limitation. The contact may be characterized by culturing an antigen and an artificial antigen presenting cell for a certain period of time.

As used herein, the term "antigen" is well known in the art, and includes not only all the molecules capable of binding to antibodies, but also epitopes, peptide fragments of antigens capable of binding to MHC molecules, and immunogens. In the present invention, as the antigen, a tumor antigen, a pathogenic antigen, an auto-antibody (normal or pathological), or the like are used, but the antigen is not limited thereto.

The tumor antigen refers to an antigen associated with tumors as a tumor associated antigen (TAA). Examples of well-known TAAs include ovalbumin, survivin, gp75, gp1OO, MDM2, MART-1, MAGE-1, MAGE-3, tyrosinase, telomerase, her-2/neu, α-1 fetoprotein, G250, NY-ESO-1, and the like. Sequences of some peptides fragments of the TAA binding to MHC molecules include $Ova_{257}$ (SIINFEKL: SEQ ID NO: 9), tyrosinase-related protein $1_{455}$ ($Trp1_{455}$; TAPDNLGYA: SEQ ID NO: 10), $Trp2_{180}$ (SVYDFFVWL: SEQ ID NO: 11), and $gp100_{25}$ ($gp100_{25}$; EGSRNQDWL: SEQ ID NO: 12), a MAGE 1 nonapeptide (EADPTGHSY: SEQ ID NO: 13), a MART-APL peptide (LAGIGILTV: SEQ ID NO: 14), a natural peptide (AAGIGILTV: SEQ ID NO: 15) or a PSA-1 peptide (FLTPKKLQCV: SEQ ID NO: 16), and the like. Additional sequences of the tumor associated peptides and antigens are known to those skilled in the art.

Examples of tumors associated with the tumor antigen include a solid tumor, a liquid tumor, a hematologic tumor, renal cell cancer, melanoma, breast cancer, prostate cancer, testicular cancer, bladder cancer, ovarian cancer, cervical cancer, stomach cancer, esophageal cancer, pancreatic cancer, lung cancer, neuroblastoma, glioblastoma, retinoblastoma, leukemia, myeloma, lymphoma, hepatoma, adenocarcinoma, sarcoma, a malignant tumor (carcinoma), blastoma, and the like.

The pathogenic antigen refers to any disease-causing organism or virus and also to attenuated derivatives thereof. The term "pathogen" refers to any virus or organism which is involved in the onset of a disease and also to attenuated derivatives thereof. Such pathogens include bacterial, protozoan, fungal and viral pathogens, for example, *Helicobacter* sp., for example, *Helicobacter pylori*, *Salmonella* sp., *Shigella* sp., *Enterobacter* sp., *Campylobacter* sp., various mycobacteria, for example, *Mycobacterium leprae*, *Mycobacterium tuberculosis*, *Bacillus anthracis*, *Yersinia pestis*, *Francisella tularensis*, *Brucella* sp., *Leptospira interrogans*, *Staphylococcus* sp., for example, *S. aureus*, *Streptococcus* sp., *Clostridum* sp., *Candida albicans*, *Plasmodium* sp., *Leishmania* sp., *Trypanosoma* sp., human immunodeficiency virus (HIV), hepatitis C virus (HCV), human papilloma virus (HPV), cytomegalovirus (CMV), HTLV, herpes virus (for example, herpes simplex virus type 1, herpes simplex virus type 2, coronavirus, varicella-zoster virus, and Epstein-Barr virus), papilloma virus, influenza virus, hepatitis B virus, poliomyelitis virus, measles virus, mumps virus, rubella virus, or the like, but are not limited thereto.

Examples of the auto-antibody include an anti-nuclear antibody, an anti-γ-globulin antibody, an antibody against an auto-blood component, an antibody against an auto-organ, or the like, but are not particularly limited thereto. When the auto-antibody is used as a foreign antigen, the CD4 T cell vaccine may induce potent anti-tumor immunity, and, thus, it can be effective for overcoming potential immunological tolerance to a self-antigen expressed in normal tissue.

The artificial antigen presenting cells sensitized with the antigen of the present invention are characterized in that the artificial antigen presenting cells induce proliferation of antigen-specific CD8+ T cells and directly stimulate CD8+ T cells, or when an HLA null 293T cell line and the artificial antigen presenting cells are washed after being co-cultured, afterward treated with the antigen, co-stimulatory molecules and HLA expressed in the artificial antigen presenting cells are transferred to the HLA null 293T cell line, and the HLA null 293T cell line may stimulate CD8+ T cells, and thus may indirectly stimulate CD8+ T cells by transferring a surface substance to other cells.

The stimulation of CD8+ T cells by the artificial antigen presenting cells is similar to the level of dendritic cells.

Since the artificial antigen presenting cell of the present invention is sensitized with a foreign antigen while overexpressing co-stimulatory molecules to improve an antigen-specific T cell response, the artificial antigen presenting cell is effective for treating tumors, pathogenic infections, or autoimmune diseases according to the type of foreign antigen.

Accordingly, the present invention provides an immunotherapeutic agent including the artificial antigen presenting cell sensitized to one or more antigens selected from the group consisting of a tumor antigen, a pathogenic antigen, and an auto-antibody.

The immunotherapeutic agent according to the present invention may increase an immune response or selectively elevate a portion of the immune response preferred for the treatment or prevention of a specific disease, infection or disorder.

Based on this, the present invention provides a vaccine or pharmaceutical composition for preventing tumors, pathogenic infections, or autoimmune diseases, including the artificial antigen presenting cell.

For example, examples of the tumor include renal cell tumor, melanoma, chronic lymphocytic leukemia, breast cancer, lung cancer, prostate cancer, ovarian cancer, colorectal cancer, or the like, but are not particularly limited thereto.

Preferred examples of the pathogenic infection include HIV, HCV, and the like, but are not particularly limited.

Preferred examples of the autoimmune disease include systemic lupus erythmatosus (SLE), rheumatoid arthritis (RA), rheumatoid fever, and the like, but are not particularly limited thereto.

The vaccine of the present invention may include all immunization methods performed by single administration and immunization methods performed by continuous administration.

The pharmaceutical composition may include an active ingredient with a pharmaceutically acceptable carrier, active or inert, making the composition suitable for diagnostic or therapeutic use in vitro, in vivo or ex vivo.

The pharmaceutically acceptable carrier includes any pharmaceutical carrier compatible with T cells, such as a phosphate buffered saline solution and a protein excipient including serum albumin such as human serum albumin (HSA), recombinant human albumin (rHA), gelatin, casein, and the like. For an example of carriers, stabilizers and adjuvants, Martin REMINGTON'S PHARM. SCI, $18^{th}$ Ed. (Mack Publ. Co., Easton (1995)) and the "PHYSICIAN'S DESK REFERENCE", 58nd Ed., Medical Economics, Montvale, N.J. (2004) are referenced. The term "carrier" may include a buffer or a pH adjusting agent, and typically, the buffer is a salt prepared from an organic acid or base. A representative buffer includes organic acid salts such as salts of citric acid, salts of ascorbic acid, salts of gluconic acid, salts of carbonic acid, salts of tartaric acid, salts of succinic acid, salts of acetic acid, or salts of phthalic acid; Tris, tromethamine hydrochloride, or phosphate buffers. An additional carrier includes a polymeric excipient/additive such as polyvinylpyrrolidone, Ficoll (a polymeric sugar), dextrate (for example, cyclodextrin, for example, 2-hydroxypropyl-quadrature, -cyclodextrin), polyethylene glycol, an antioxidant, an antistatic agent, a surfactant (for example, a polysorbate such as "TWEEN 20" and "TWEEN 80"), a lipid (for example, phospholipid, fatty acid), a steroid (for example, cholesterol), and a chelating agent (for example, EDTA). Agents for preventing or inhibiting freezing may also be included.

The pharmaceutical composition of the present invention may be prepared in various formulations as appropriate. For example, a formulation suitable for parenteral administration, such as by intratumoral, intraarterial (in the joints), intravenous, intramuscular, intradermal, intraperitoneal, intranodal and subcutaneous routes, and a carrier include an antioxidant, a buffer, a bacteriostat, and a solute that renders the formulation isotonic with the blood of an intended recipient, and an aqueous and non-aqueous sterile suspension that may include a suspending agent, a solubilizer, a thickening agent, a stabilizer, and a preservative. Intravenous or intraperitoneal administration is a preferred method. The dose of cells administered to an individual is an amount which is effective to achieve a desired beneficial therapeutic response in the individual over time, or to inhibit growth of cancer cells, or to inhibit infection. For example, the administration may be performed by a method of obtaining and storing a blood sample from an individual prior to injection and using the blood samples for subsequent analysis and comparison. In general, at least about $1 \times 10^4$ to $1 \times 10^6$ and typically, $1 \times 10^8$ to $1 \times 10^{10}$ cells may be injected intravenously or intraperitoneally into a 70 kg patient over roughly 60 to 120 minutes. For administration, cells of the present invention are administered at a rate determined by the LD-50 (or other methods of measuring toxicity) according to the cell type and the side-effects according to the cell type at various concentrations, in consideration of the overall health status and body weight of the individual. Administration may be accomplished via single or divided doses. The artificial antigen presenting cell of the present invention may supplement other treatments for a specific condition using a known conventional therapeutic method including a cytotoxic agent, a nucleotide analog and a biologic response modifier. Similarly, the biological response modifier may be optionally added to treatment by the artificial antigen presenting cell of the present invention.

Further, the present invention provides a method for treating tumors, pathogenic infections, or autoimmune diseases, including a step of administering a pharmaceutical composition containing the artificial antigen presenting cell sensitized to one or more antigens selected from the group consisting of a tumor antigen, a pathogenic antigen, and an autoantibody to a subject in need thereof.

Since the pharmaceutical composition and administration method used for the method for treating tumors, pathogenic infections, or autoimmune diseases were described above, the descriptions of overlapping contents therebetween will be omitted to avoid excessive complexity of the present specification.

Meanwhile, the subject to which the composition for treating tumors, pathogenic infections, or autoimmune diseases may be administered includes all animals. For example, the animal may be a mammal such as a human, a pig, a gorilla, a monkey, a dog, a cat, and a rat.

The types of tumors, pathogenic infections, or autoimmune diseases are the same as those described above.

The present invention also provides a method for in vitro proliferating cytotoxic T cells, including a step of co-culturing the artificial antigen presenting cell sensitized to one or more antigens selected from the group consisting of a tumor antigen, a pathogenic antigen, and an autoantibody with any one T cell of a CD4+T cell, a CD8+T cell, or a γδT cell.

The artificial antigen presenting cell of the present invention may proliferate the T cells when co-cultured with the CD4+ T cell, the CD8+ T cell, or the γδT cell. In addition, when the T cells are stimulated by an artificial antigen presenting cell sensitized with an antigen, antigen-specific cytotoxic T cells may be produced.

The stimulation or co-culturing of the CD4+ T cell, the CD8+ T cell, or the γδT cell by the artificial antigen presenting cell is performed in a cell culture medium supplemented with interleukin-2 (IL-2) in the absence of an immune stimulatory ligand.

The cell culture medium may be a safe medium for animal cell culture. Examples of the safe medium include Dulbecco's Modified Eagle's Medium (DMEM), Minimal Essential Medium (MEM), Basal Medium Eagle (BME), RPMI1640, F-10, F-12, α-Minimal Essential Medium (α-MEM), Glasgow's Minimal Essential Medium (GMEM), Iscove's Modified Dulbecco's Medium, and the like, but are not limited thereto.

The IL-2 may be added at a concentration of 20 to 100 IU/mL.

The stimulation by using the artificial antigen presenting cell may be performed for 4 days to 10 days, but the period is not particularly limited thereto.

The culture conditions may include a flow rate of 5 to 15% carbon dioxide and 35 to 37° C. in a $CO_2$ incubator, but are not particularly limited thereto.

Hereinafter, the present invention will be described in more detail through the Examples according to the present invention, but the scope of the present invention is not limited by the Examples suggested below.

EXAMPLES

<Example 1> Preparation of HLA Class I Null 293T Cell Line-Based Artificial Antigen Presenting Cell An HLA null 293T cell line was established, and an artificial antigen presenting cell expressing HLA and various co-stimulatory molecules was prepared based on this.
(Cell Culture)

HEK 293T cells were cultured in a DMEM medium supplemented with 10% fetal bovine serum (FBS), 1% L-glutamine, and 1% penicillin-streptomycin. T2 cells were cultured in an RPMI-1640 medium supplemented with 10% FBS, 1% L-glutamine, and 1% penicillin-streptomycin.
(Flow Cytometry)

Target cells were stained with an anti-human antibody labeled by fluorescence for 30 min at room temperature in a dark room as follows: CD80-BV605 (L307.4, BD Bioscience), CD32-APC (FLI8.26, BD Bioscience), CD83-PerCP-CY5.5 (HB15e, Biolegend), CD137L-PE (5F4, Biolegend), CD54-Pacific Blue (HCD54, Biolegend), CD70-FITC (Ki-24, BD Bioscience), HLA-ABC-APC (G46-2.6, BD Bioscience) or HLA-ABC-PE (W6/32, Biolegend), HLA-A0201-PE (BB7.2, Biolegend), CD3-FITC (OKT3, Biolegend), CD8-PerCP-CY5.5 (RPA-T8, Biolegend), MART 26-35 Tetramer-PE (A*02:01 ELAGIGILTV, Proimmune; SEQ ID NO: 7), CD45RO-PE-Cy7 (UCHL1, Biolegend), CCR7-APC-Cy7 (G043H7, Biolegend), CD62L-APC (DREG-26, BD Bioscience), CD56-BV421 (NCAM16.2, BD Bioscience). Stained cells were analyzed by measuring the degree of fluorescence expression using FACS Canto or Fortessa (BD Bioscience).
(gRNA Design and Construction)

Total six gRNAs targeting each of HLA-A exon 2 (AE2: GAGCCAGAGGATGGAGCCGCGGG: SEQ ID NO: 1), A exon 3 (AE3: GAAGGAGACGCTGCAGCGCACGG: SEQ ID NO: 2), B exon 2 (BE2: GCTGTCGAACCT-CACGAACTGGG: SEQ ID NO: 3), B exon 3 (BE3: GAG-CATGTACGGCTGCGACGTGG: SEQ ID NO: 4), C exon 2 (CE2: GACACAGAAGTACAAGCGCCAGG: SEQ ID NO: 5), and C exon 3 (CE3: CCAGAG-GATGTCTGGCTGCGACC: SEQ ID NO: 6) were encoded in pSpCas9 BB-2A-GFP or Puro all-in-one plasmids obtained from Genscript (PX458, PX459).
(Transfection for Multiplex Gene Editing)

HEK 293T cells were seeded at $2\times10^6/10$ ml cells in an antibiotics-free DMEM medium. 24 h later, 293T cells were co-transfected with each of HLA-A, -B, -C targeted six gRNAs encoded in all-in-one plasmids using Lipofectamine (Invitrogen). 48 h post-transfection, cells were analyzed by flow cytometry. 6 days post-transfection, HLA-A, -B, -C negative cells were sorted and single cell clones were established.
(FACS Sorting and Single Cell Cloning)

For establishment of an HLA-A, -B, -C null cell line, six plasmid co-transfected cells were harvested and stained with Rinsing Solution (Miltenyi Biotec) and HLA-ABC-APC Ab (G46-2.6, BD Bioscience) at room temperature for 30 min. Live, GFP negative, HLA-ABC negative 293T cells were sorted and single cells seeded on 96 well plates using Moflo XDP cell sorters (Beckman). For the individual HLA-expressing cell or co-stimulatory molecule-expressing cell, each molecule-transfected cell was stained with HLA-ABC-PE Ab (W6/32, Biolegend) or CD83-PerCP-CY5.5 Ab (HB15e, Biolegend). Also, each positive cell was sorted and single cell seeded on 96 well plates using Moflo XDP cell sorters (Beckman). 2 to 3 weeks post-sorting, single cell clones were established.
(Single Cell PCR, Electrophoresis and Sanger Sequencing)

2 to 3 weeks post-sorting, HLA-A, -B, -C negative single cell clones were established and cultured on 6 well plates (n=188). Clonal genomic DNA was isolated from each of $1\times10^5$ to $10^6$ clones using TIANamp Genomic DNA Kit (TIANGEN) according to the manufacturer's instructions. Also, target regions were amplified in HLA-A, -B, -C exon 2 and 3 by using specific primers and protocols in the lab. PCR products were analyzed by electrophoresis with 2% agarose gel, SYBR Green, and a 100 bp ladder (Bioneer) for screening of predicted large deletion clones. Finally, PCR products of selected clones were analyzed by Sanger sequencing (Cosmo Genetech) using the same primers.
(Lentivirus Production and Transduction)

For production of lentiviruses encoding the respective molecules (HLA-A*02:01, A*02:06, B*07:02, B*40:06, CD80-T2A-CD32, CD83-T2A-CD137L, CD54, and CD70), $5\times10^6/10$ ml of 293T cells were seeded in a T75 flask. 24 h later, 10 μg of a cloned pCDH plasmid (SBI) and lentivirus packaging plasmids (5 μg psPAX2 and 5 μg pMD2G) were co-transfected into 293T cells using Lipofectamine (Invitrogen). 48 h post-transfection, a supernatant was harvested and filtered through a 0.45 μM filter. For transduction of each lentivirus, $5\times10^5$/ml 293T cells were seeded on 6 well plates. 24 h later, 293T cells were treated with a 500 μl lentiviral supernatant and 8 μg/ml polybrene. 48 h post-transduction, cells were cultured and flow cytometry was performed. 6 days post-transduction, positive cells were sorted and clones were established.
(Isolation of CD8+T Cells)

Mononucleocytes were isolated using Ficoll-Hypaque (Amersham Pharmacia Biotech) density gradient centrifugation and cryopreservation. Following density separation, CD8+T cells were isolated according to the manufacturer's instructions using MACS System (Miltenyi Biotec). Isolated CD8+T cells were used for enzyme-linked immunospot (ELISPOT) assay and antigen specific cytotoxic T cell generation.
(Enzyme-Linked Immunospot Assay)

For detection of cells secreting interferon-γ (IFN-γ), ELISPOT assays were performed according to the manufacturer's instructions using a BD ELISPOT assay kit. For individual HLA functional experiments, the CD8 T cells isolated from individual HLA matched healthy donors ($1\times10^6$ cells) were serially diluted in complete RPMI and 100 μl of each concentration was transferred into the wells, followed by the addition of 200 μl of non-transfected or transfected target cells ($1\times10^5$ cells) with a piggy-bac-pp65 whole Ag-GFP vector (SBI) to the complete RPMI. A $1\times10^5$ CD8 T cells/well condition was run in duplicate. The number of IFN-γ spots was counted using AID-ELISPOT-Reader (AID). For functional experiments of antigen specific CTLs, the MART-1 specific CTLs ($2.5\times10^5$ cells) or pp65 specific CTLs ($2.5\times10^5$ cells) were serially diluted in complete RPMI and 125 μl of each concentration was transferred into the wells, followed by the addition of 250 μl of MART-$1_{26-35}$ peptide (ELAGIGILTV: SEQ ID NO: 7) or pp65$_{495}$ peptide (NLVPMVATV: SEQ ID NO: 8) non-pulsed or pulsed T2 cells (2.5×10⁴ cells) to the complete RPMI. The number of IFN-γ spots was counted using AID-ELISPOT-Reader (AID).

(Antigen Specific Cytotoxic T Cell Generation)

MART-1 specific cytotoxic T cells (CTLs) were generated using MART-1$_{26-35}$ peptide (ELAGIGILTV: SEQ ID NO: 7) pulsed A*02:01-293T(H1E-45)-Cos cells. pp65 specific cytotoxic T cells (CTLs) were generated using pp65$_{495}$ peptide (NLVPMVATV: SEQ ID NO: 8) pulsed 293T-Cos (+CD54, +CD70) cells. CTLs were cultured with irradiated stimulator cells at 10 U/ml IL-2 (Proleukin), and 10 ng/ml IL-15 every 6 to 7 days. Briefly, purified CD8+T cells from A*02:01 healthy donors were used as responder cells and stimulated a total of three times using irradiated (10,000 cGy), MART-1$_{26-35}$ peptide pulsed A*02:01-293T(H1E-45)-Cos or pp65$_{495}$ peptide (NLVPMVATV: SEQ ID NO: 8) pulsed 293T-Cos (+CD54, +CD70) cells as stimulator cells at a stimulator cell: responder ratio of 1:20 (first) and 1:10 (second and third). Post-first stimulation, CTLs were harvested, and viability was assessed using trypan blue. Post-second and third stimulations, CTLs were harvested, counted, and analyzed for their functional capacity.

<Example 2> Establishment of HLA Class I Negative Cell Clones

Human embryonic kidney (HEK) 293T cells were selected as a model suitable for the attempt of the present invention. The 293T cell line has beneficial features of high transfection efficiency and homologous haplotypes of HLA class I (A*02:01, B*07:02, and C*07:02). For complete elimination of HLA class 1 molecules, six plasmids that encoded a Cas9 protein and gRNAs targeting exon 2 and 3 of the respective HLA-A, -B, and -C genes were used (FIG. 1). These six plasmids were co-transfected into 293T cells. 6 days after transfection, cells showing the lowest expression of HLA class 1 molecules by staining with an HLA class 1 molecule specific antibody (HLA-ABC-APC, G46-2.6, BD Bioscience) were sorted and single cell seeded on 6-well plates or 8 of 96-well plates (FIG. 1). When the whole sorted cells on 6-well plates were cultured for 10 days, the proportion of HLA class 1 negative cell groups was 42.7% (FIG. 1). At 2 to 3 weeks after sorting, 188 clones (24.5%) among total 768 wells were cultured and were analyzed for HLA class I gene mutation and expression.

Figure 2A:
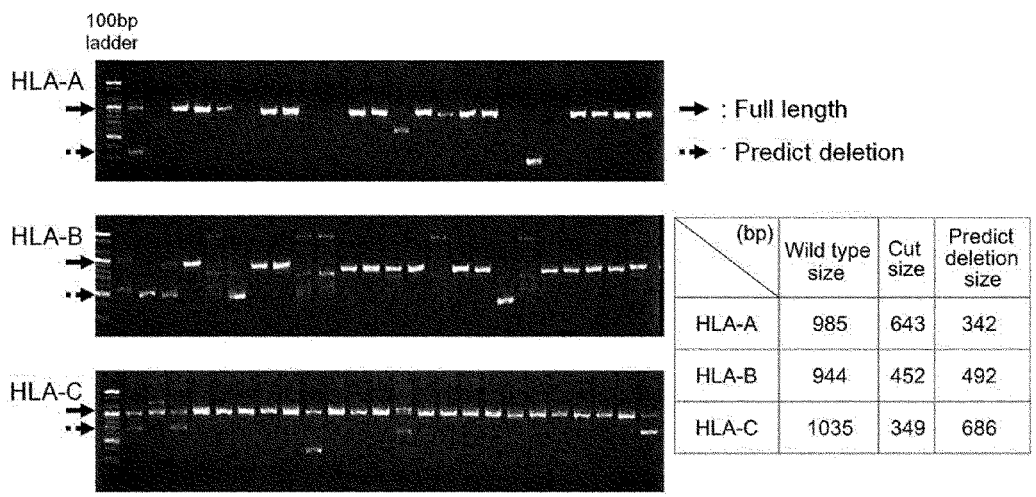
FIGS. 2a and 2b are mutation frequency analysis results in single cell clones using target specific PCR and gel electrophoresis (n=188)
Figure 2B:
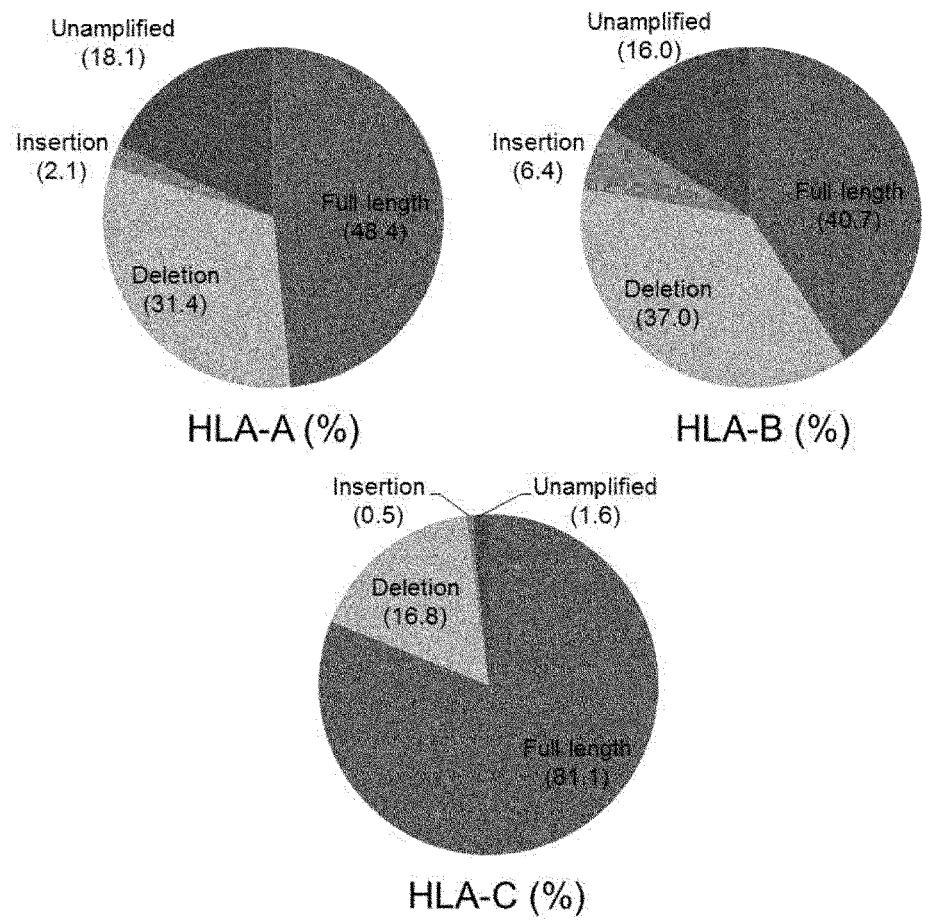

<Example 3> Genetic and Flow Cytometric Analysis for HLA Class I Negative Cell Clones For detection of induced mutations, PCR was carried out using the specific primer pairs including gRNA target regions in exon 2 and 3 of each HLA class I genes (FIG. 1). When PCR product size was changed relative to that of control cell, shorter (deletion), longer (insertion) or unamplified products were referred to as detectable changes of PCR products (DCP). When PCR products were detected as a single band or double band, they were regarded as homozygous or heterozygous (FIG. 2a). The gene frequencies of deletion and insertion mutations were 31.4% and 2.1% in HLA-A, 37.0% and 6.4% in HLA-B, and 16.8% and 0.5% in HLA-C (FIG. 2b). The unamplified product was the result of homozygous deletion, and was presumed to be the larger deletion that affected PCR. The gene frequencies of unamplified samples were 18.1% in HLA-A, 16.0% in HLA-B, and 1.6% in HLA-C (FIG. 2b). When the PCR product size was the same or similar, it was regarded as full length, which may include no mutation, or substitution or small insertions or deletions. These results demonstrated that the mutations of HLA-B, HLA-A, and HLA-C frequently occur in order. The mutation frequencies at each HLA class I locus may represent the efficiency of gRNA targeting each HLA class I locus.

Figure 3A:
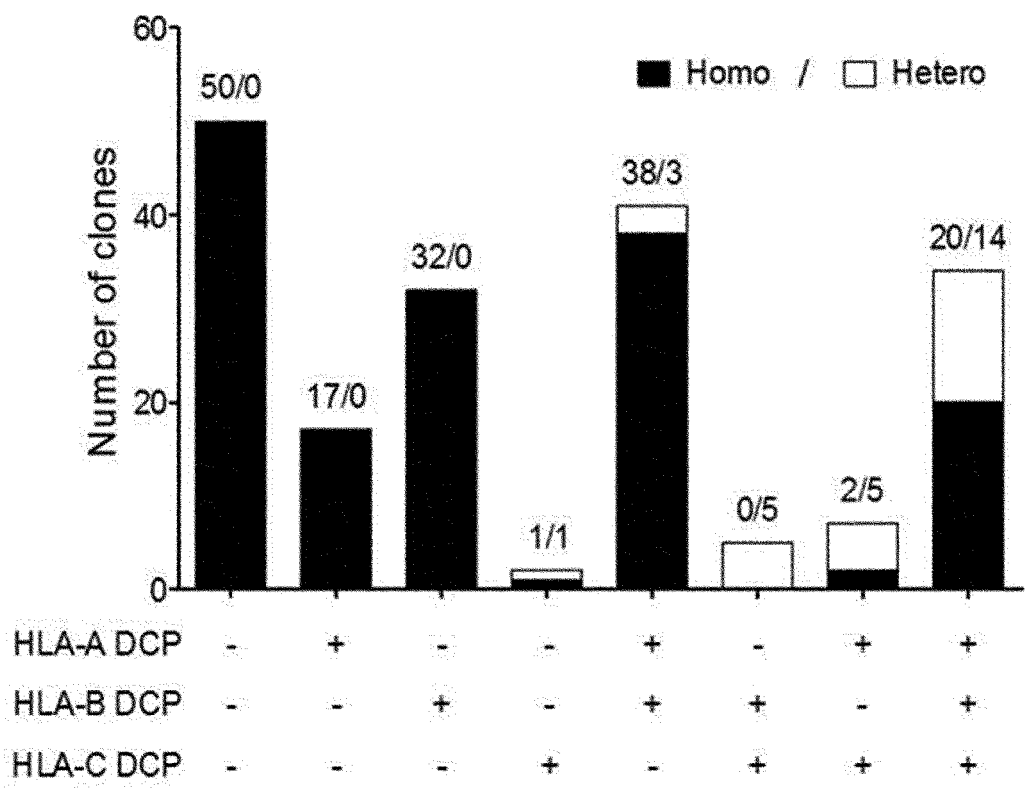
FIGS. 3a to 3c illustrate genotype, expression level and sequencing analysis results of clones.

Among the cultured 188 clones, 50 clones (26.6%) did not show any DCP at 3 HLA class I loci. 17 clones (9.0%) showed DCP in only HLA-A, 32 clones (17.0%) in only HLA-B, and 2 clones (1.1%) in only HLA-C. DCP at both HLA-A and -B loci were detected in 41 clones (21.8%), DCP at both HLA-B and -C loci in 5 clones (2.7%), and DCP at both HLA-A and -C loci in 7 clones (3.7%). 34 clones showed 20 homozygous DCP (10.6%) and 14 heterozygous DCP (7.5%) at all HLA class I loci (FIG. 3a).

Figure 3B:
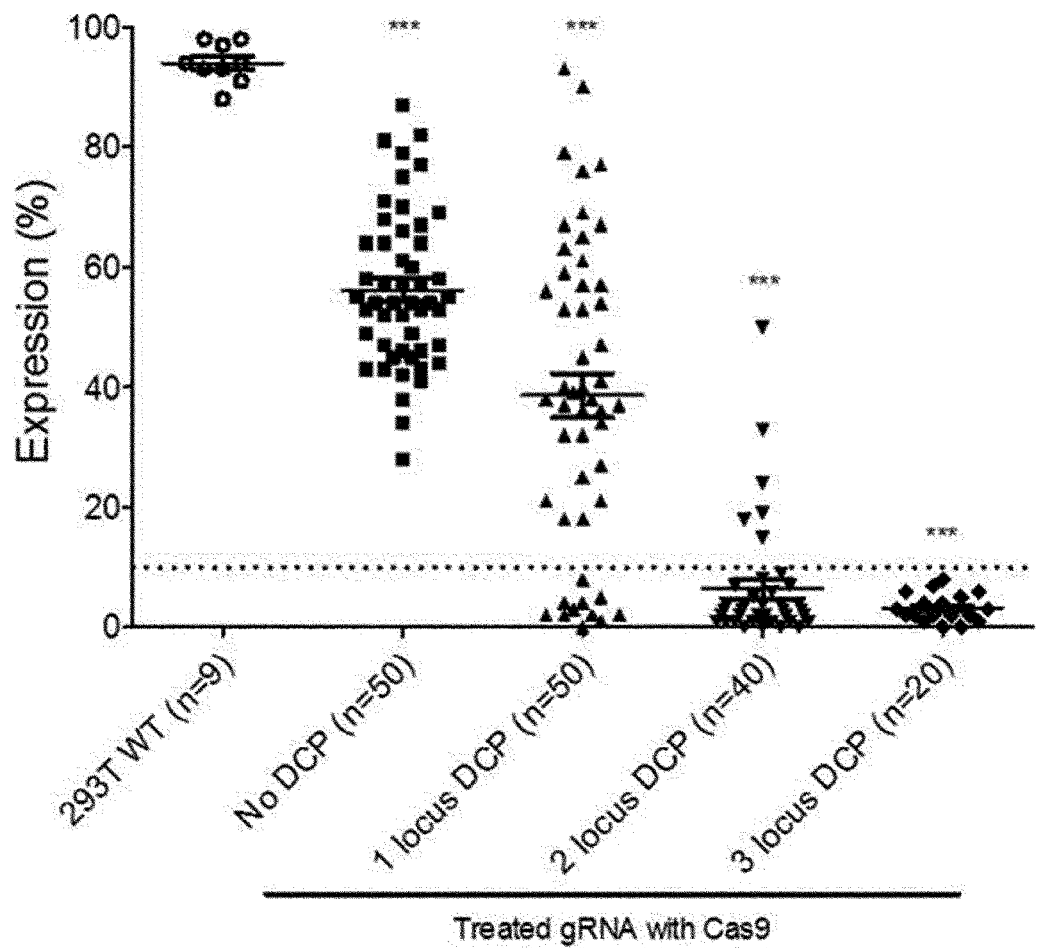

The HLA class I expression was analyzed according to distribution of DCP at HLA class I loci in homozygous clones (FIG. 3b). When the highest intensity level in the unstained HEK 293T cells was used as a cut off value for HLA class I expression, 94.0% of wild type HEK 293T cells were determined as positive for HLA class I expression. The mean positive ratio in a DCP-free group was 56.2%, 38.6% in a 1 locus DCP group, 6.4% in a 2 loci DCP group, and 3.2% in a 3 loci DCP group (FIG. 3b). The lower HLA class I expression in the DCP-free group than in the control suggested the presence of small insertions or deletions by a single gRNA effect. These results demonstrated the decrease in HLA class I expression depending on the number of DCP alleles (FIG. 3b).

Figure 3C:
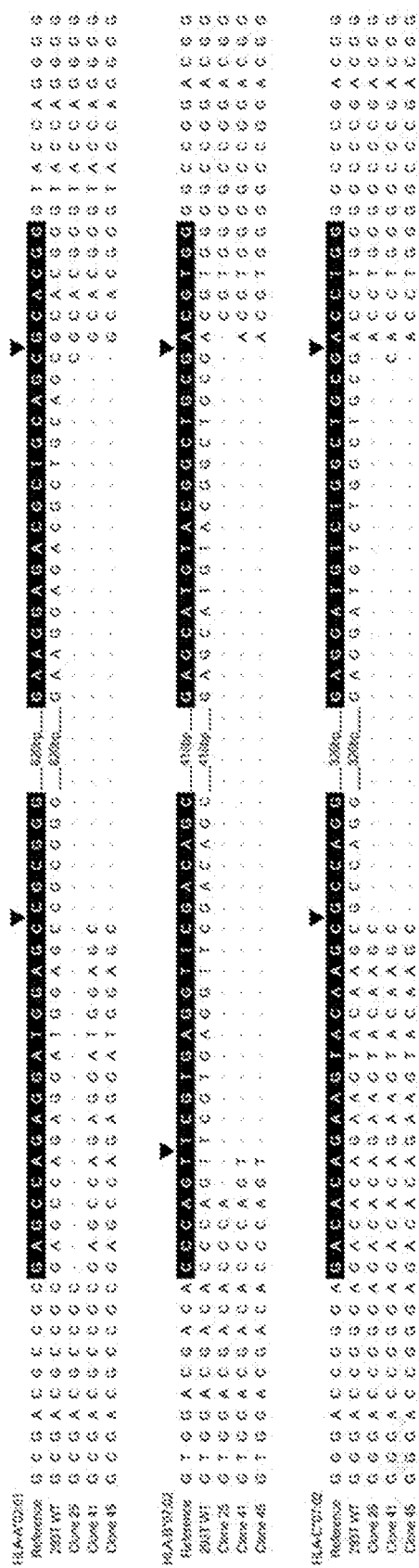

For selection of an HLA-A, -B, -C null 293T cell line, the nucleotide sequences were confirmed in 3 homozygous clones that had predicted deletions in HLA-A, -B, and -C genes (FIG. 3c). All 3 clones showed large deletions between regions close to two expected cleavage sites at each targeted HLA class I locus. In next experiments, the clone 45 (null-293T(H1E-45)) was used for the development of AAPC.

Figure 4A:
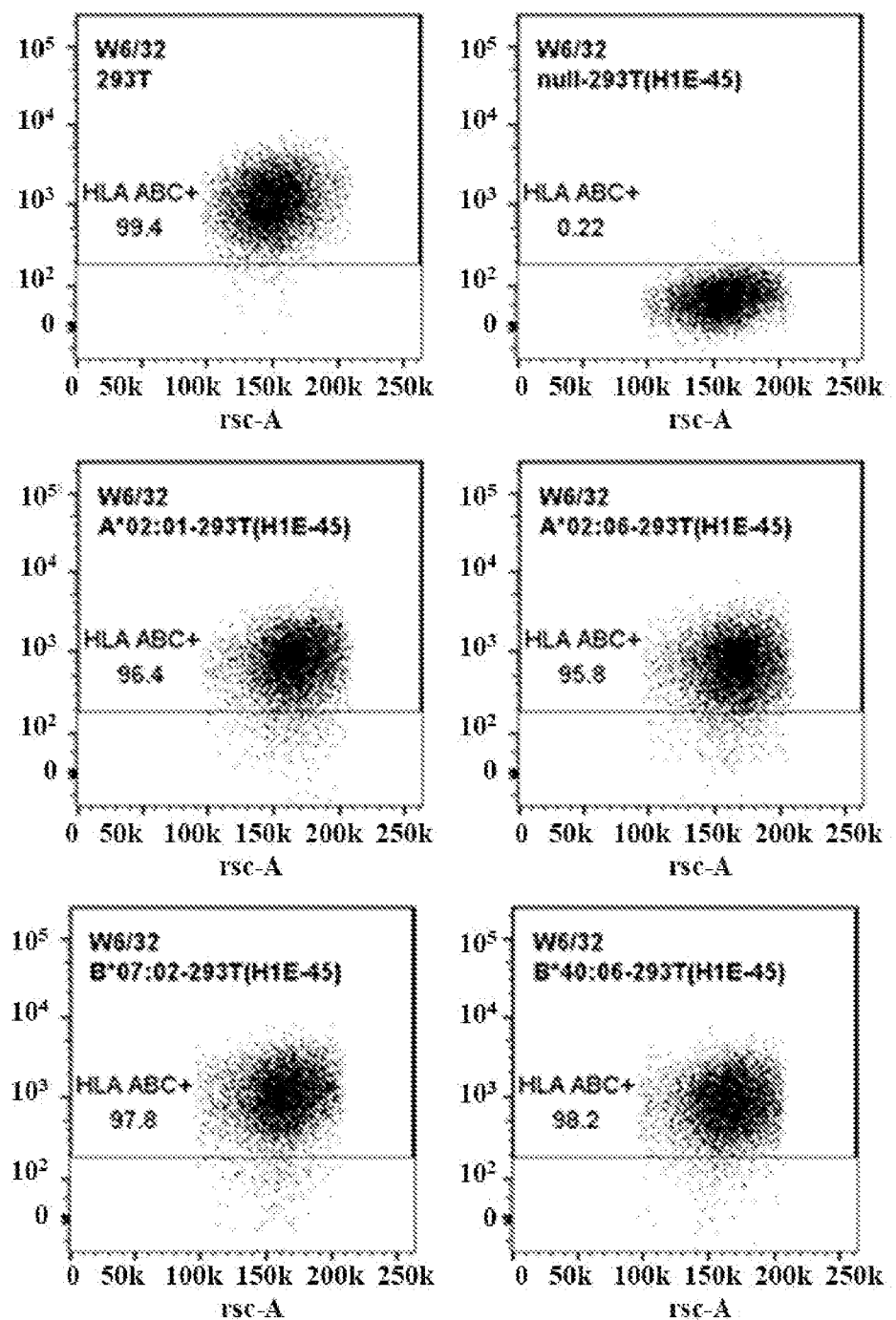
FIGS. 4a and 4b illustrate functional test results with respect to the removal and restoration of HLA class I molecules in an HLA class I null cell line using lentiviral transduction and ELISPOT assay.

<Example 4> Antigen Presentation by Transferred Single HLA Class I Gene into HLA Class I Null 293T Cell Line To demonstrate antigen presentation and natural antigen processing in restricted single HLA class I alleles in the null-293T(H1E-45), HLA class I positive cells were sorted at 6 days after transfection of the null-293T(H1E-45) cell line with HLA-A*02:01, A*02:06, B*07:02, or B*40:06. A*02:01-, A*02:06-, B*07:02-, and B*40:06-293T(H1E-45) cells showed the HLA class I of 95% or more by flow cytometry (FIG. 4a). Afterward, the plasmid expressing the CMV pp65 whole antigen was transfected into wild type 293T, null-, A*02:01-, A*02:06-, B*07:02-, and B*40:06-293T(H1E-45) cells. The IFN-γ enzyme-linked immunospot (ELISPOT) assay were carried out on CD8+T cells from HLA matched donors.

Figure 4B:
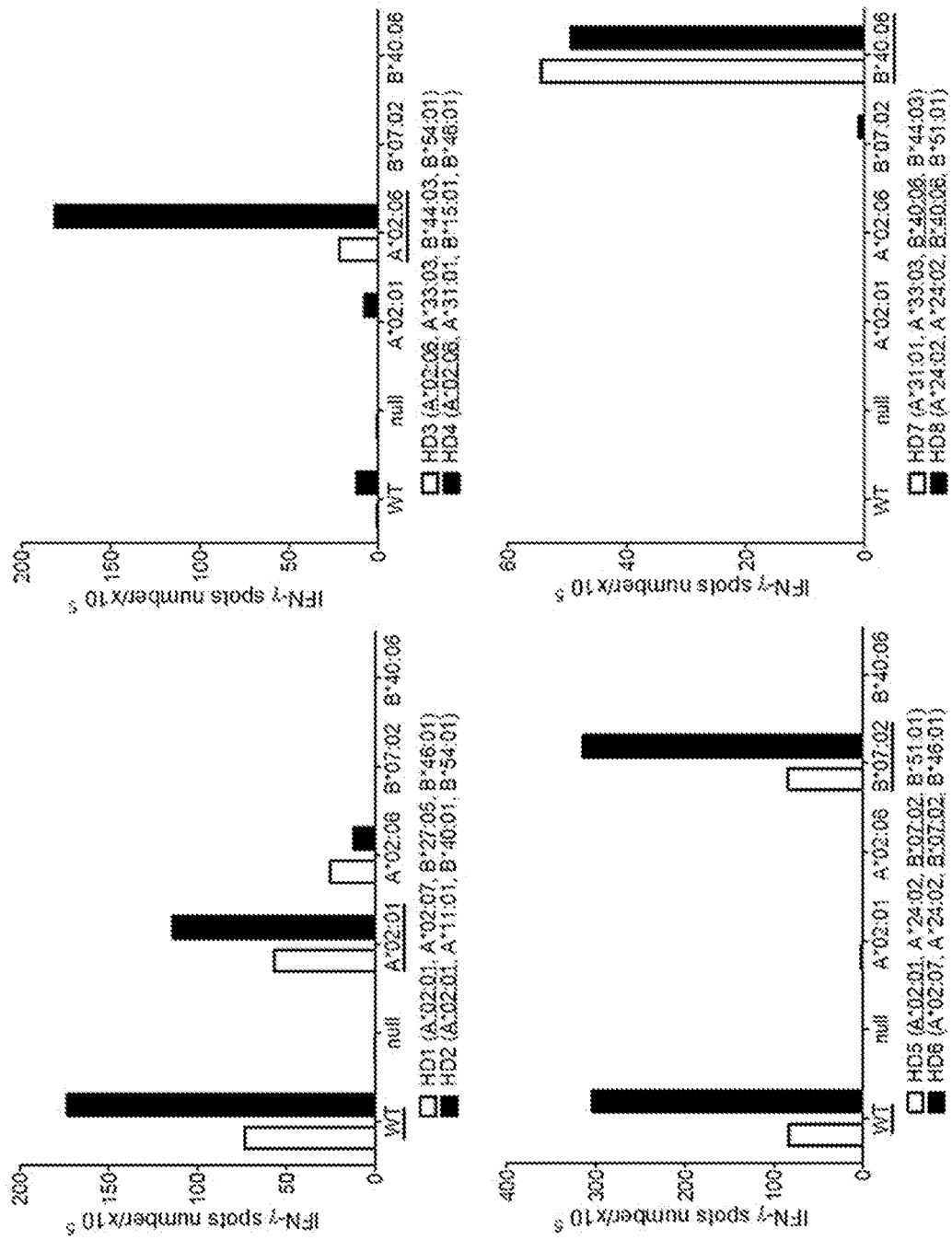

In the CD8+T cells from HLA-A*02:01 matched HD1 and HD2 donors, each of 73.5 and 173 IFN-γ spots occurred in wild type 293T wells and each of 56.5 and 114 spots occurred in A*02:01-293T(H1E-45) wells (FIG. 4b). In CD8+T cells from HLA-A*02:06 matched HD3 and HD4 donors, each of 22 and 181.5 spots occurred in A*02:06-293T(H1E-45) wells (FIG. 4b). In the CD8+T cells from HLA-B*07:02 matched H51 and HD6 donors, each of 84 and 304.5 IFN-γ spots occurred in wild type 293T wells and each of 85 and 314 spots occurred in B*07:02-293T(H1E-45) wells (FIG. 4b). In CD8+T cells from HLA-B*40:06 matched HD3 and HD4 donors, each of 54.5 and 49.5 spots occurred in B*40:06-293T(H1E-45) wells (FIG. 4b). Among all donors, 0 to 25.5 spots occurred in mismatched groups and 0 to 0.5 spots occurred in null-293T(H1E-45) groups (FIG. 4b). Also, among all donors except for HD3, positive range spots occurred in each matched group (FIG. 4b). The IFN-γ ELISPOT data showed clear results for the specific immune responses of each matched group (FIG. 4b).

From the results, two conclusions were drawn from ELISPOT data. First, this approach could eliminate and restore HLA class I molecules, and not only phenotypes, but also functions could be eliminated. Second, it could restore HLA class I molecules so as to enable natural antigen processing and presenting regardless of HLA types.

Figure 5A:
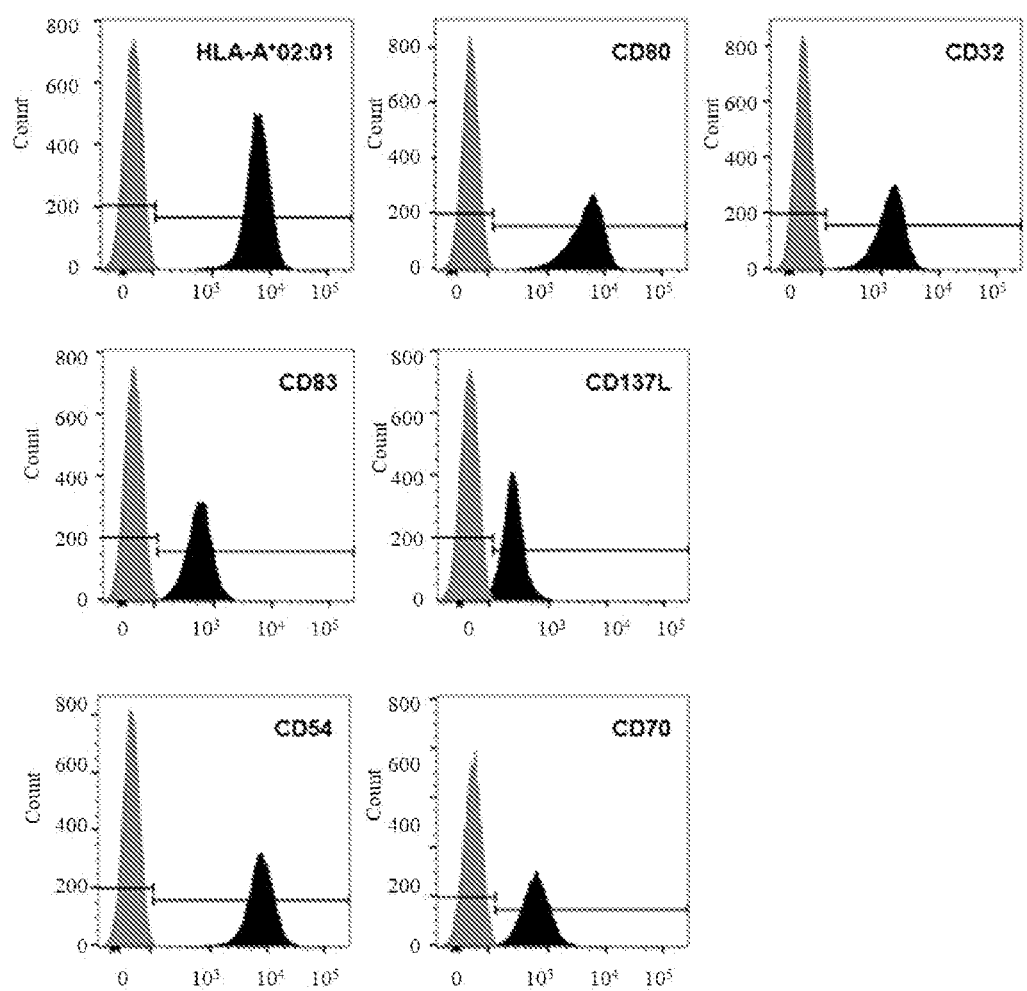
FIGS. 5a to 5c illustrate production results of MART-1 specific cytotoxic T cells stimulated by HLA-A*02:01-293T (H1E-45)-Cos (n=3)

<Example 5> In Vitro Antigen Specific Cytotoxic T Cell Generation by HLA Class I Null 293T Cell Line-Based Artificial Antigen Presenting Cell For generation of antigen specific cytotoxic T cells (CTLs), an A*02:01-293T(H1E-45)-Cos cell line which expressed HLA-A*02:01, CD80, CD32, CD83, 4-1BBL, CD54, and CD70 was established by lentiviral transduction, positive cell sorting, and single cell cloning (FIG. 5a). Afterward, a total of three stimulations was performed every 6 to 7 days and immune responses were measured on days 0, 13, and 19 with the MART-$1_{26-35}$ peptide (FIGS. 5b and 5c).

Figure 5B:
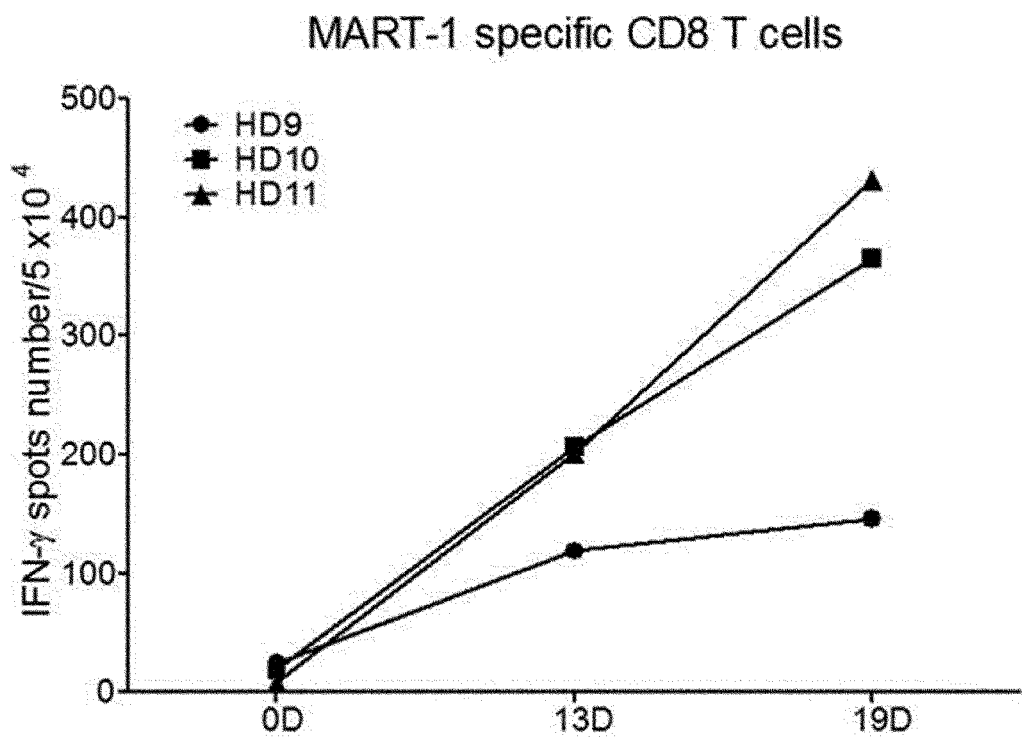
Figure 5C:
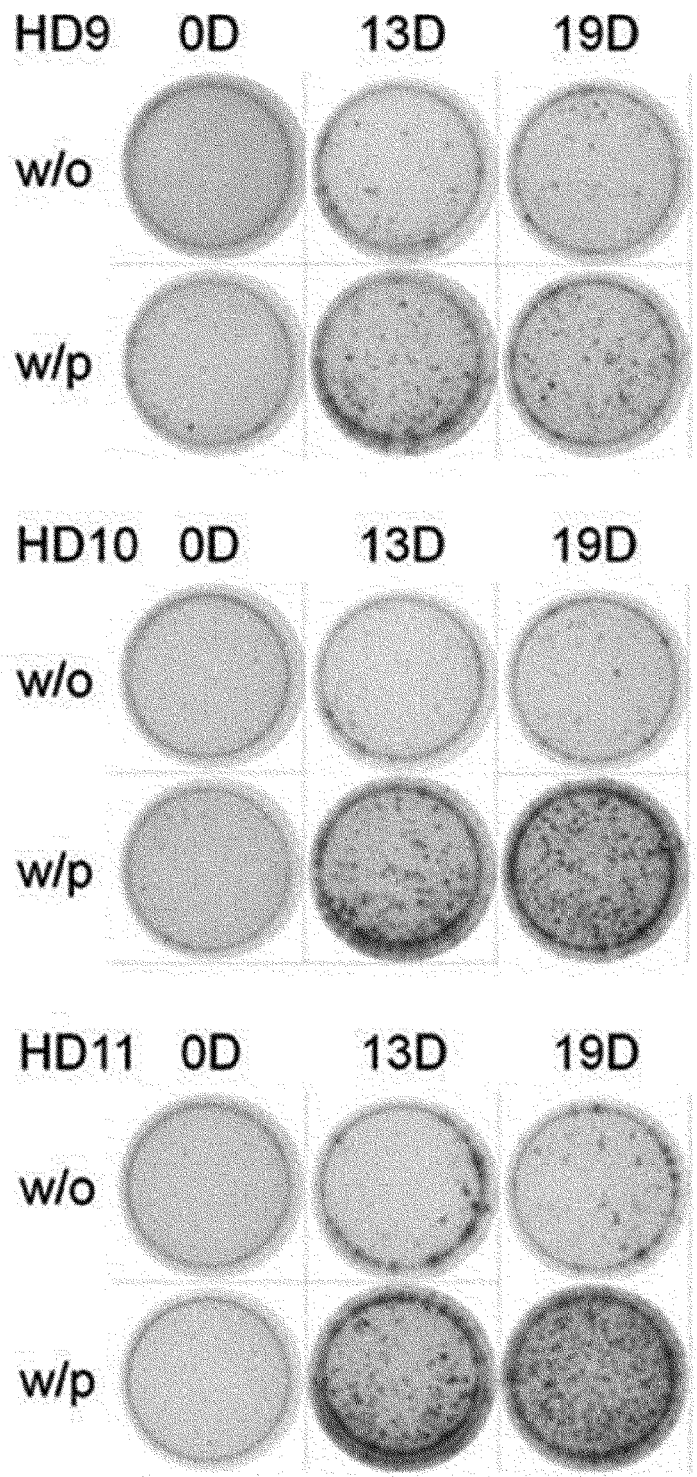

As illustrated in FIGS. 5b and 5c, the meaningful number of IFN-γ spots on days 0, 13, and 19 was 25, 119, and 146 in HD9, 19, 207, and 365 in HD10, and 8, 201, and 431 in HD11. This data showed an increase in immune responses that was 4.8- to 25.1-fold on day 13 and 5.8- to 53.9-fold on day 19.

Figure 6A:
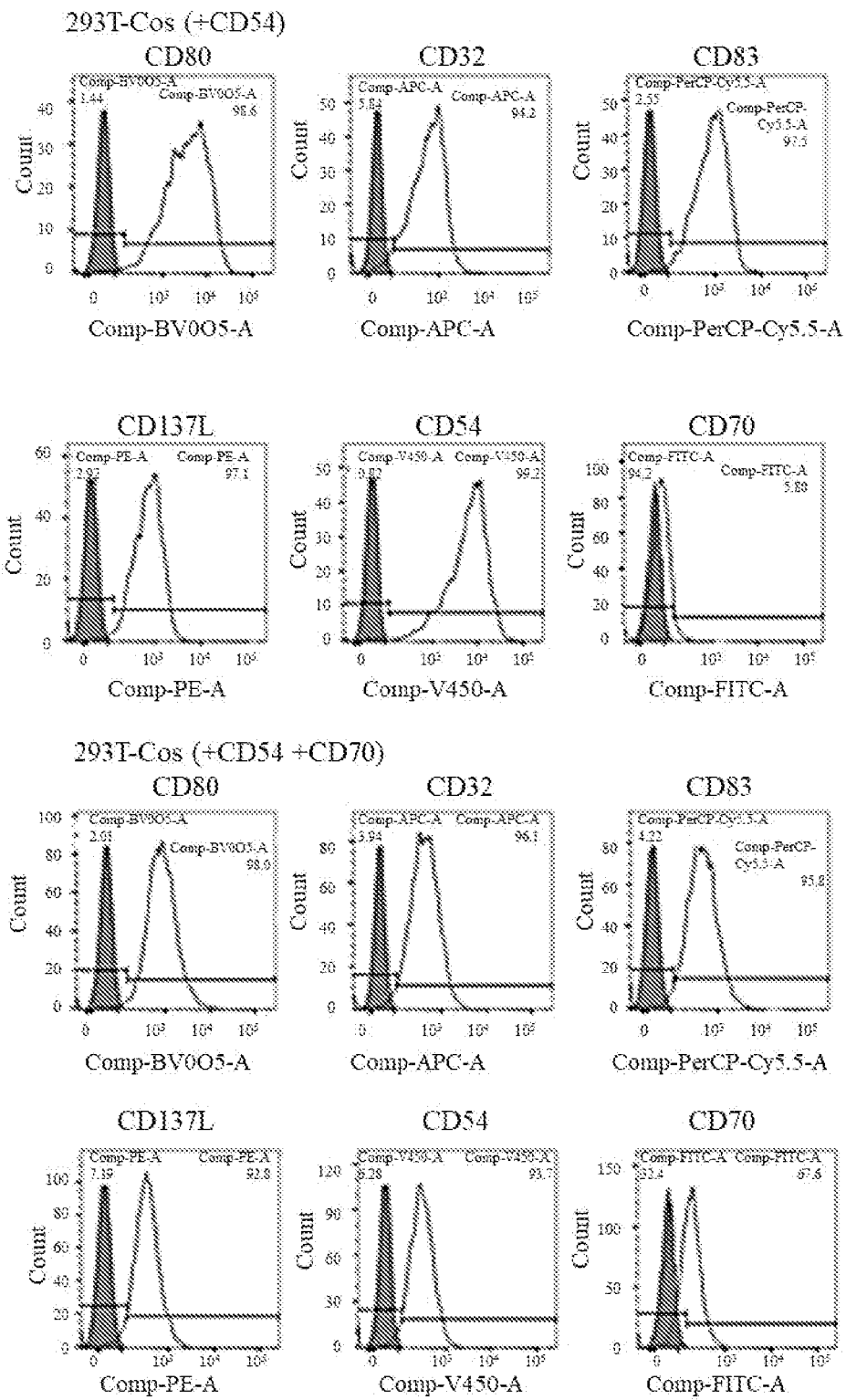
FIG. 6a is a result of measuring the expression level of HLA and the co-stimulatory molecules CD80, CD32, CD83, CD137L, CD54, and CD70 for the artificial antigen presenting cells based on 293T cells [an artificial antigen presenting cell expressing 293T-Cos(+CD54): CD80, CD32, CD83, CD137L, and CD54, and an artificial antigen presenting cell expressing 293T-Cos(+CD54, +CD70): CD80, CD32, CD83, CD137L, CD54, and CD70]
Figure 6B:
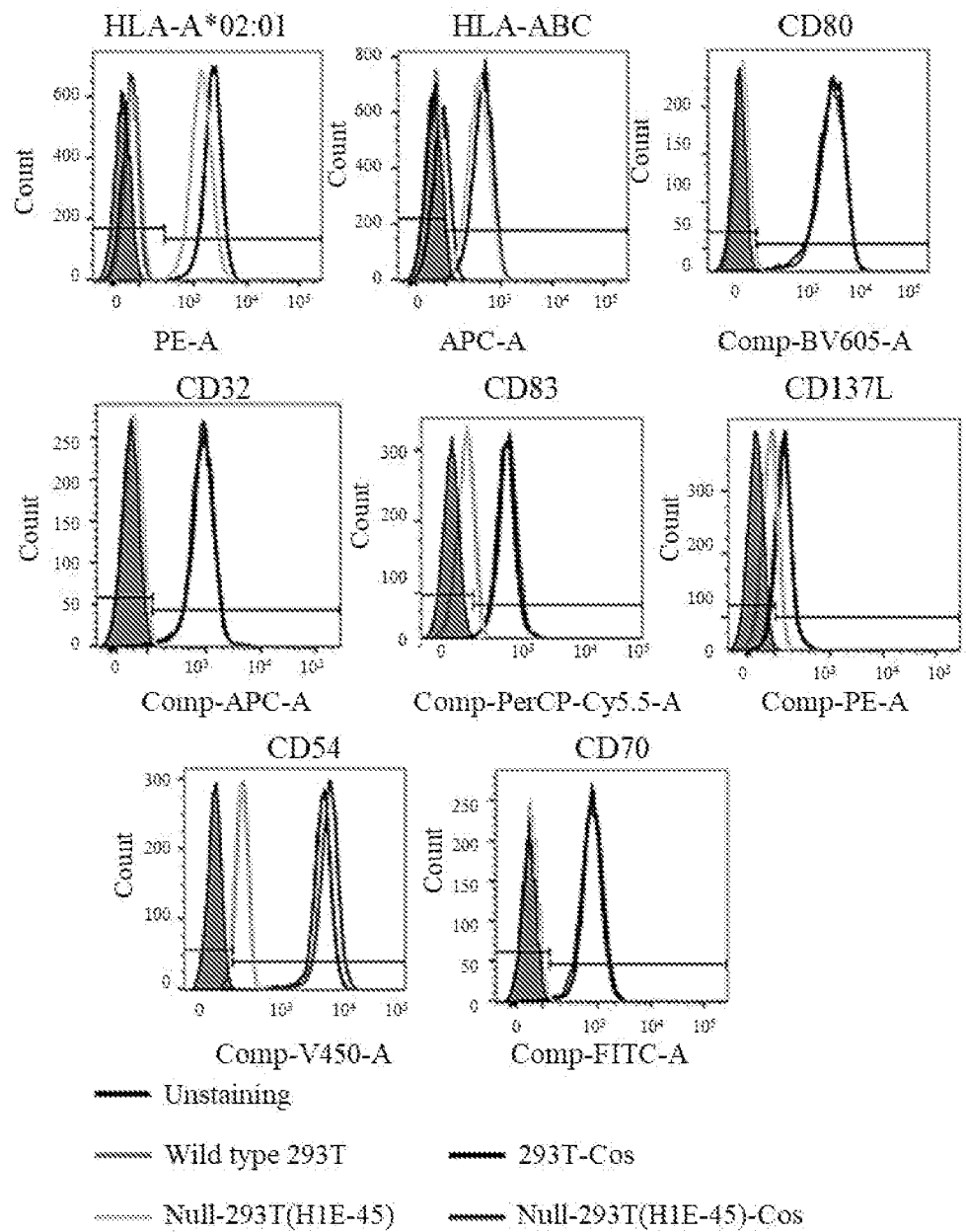
FIG. 6b is a result of measuring the expression level of HLA and co-stimulatory molecules of the artificial antigen presenting cells based on a null-293T (H1E-45) cell line.

<Example 6> Expression Level of HLA and Co-Stimulatory Molecule Group of 293T Cell-Based Artificial Antigen Presenting Cells and In Vitro Antigen Specific Cytotoxic T Cell Generation Based on 293T cells naturally expressing HLA, cell lines of 293T-Cos (+CD54: an artificial antigen presenting cell expressing CD80, CD32, CD83, CD137L, and CD54) and 293T-Cos (+CD54 +CD70: an artificial antigen presenting cell expressing CD80, CD32, CD83, CD137L, CD54, and CD70) expressing CD80, CD32, CD83, 4-1BBL, CD54, or CD70 were established by lentiviral transduction and single cell cloning, and the expression level of HLA and the co-stimulatory molecule group was measured with the HLA class I null 293T cell line-based artificial antigen presenting cell prepared in Example 5 (FIGS. 6a and 6b). Thereafter, a total of three stimulations was performed every 6 to 7 days and immune responses were measured on days 0, 13, and 19 with the pp65$_{495}$ peptide (FIG. 7).

Figure 7:
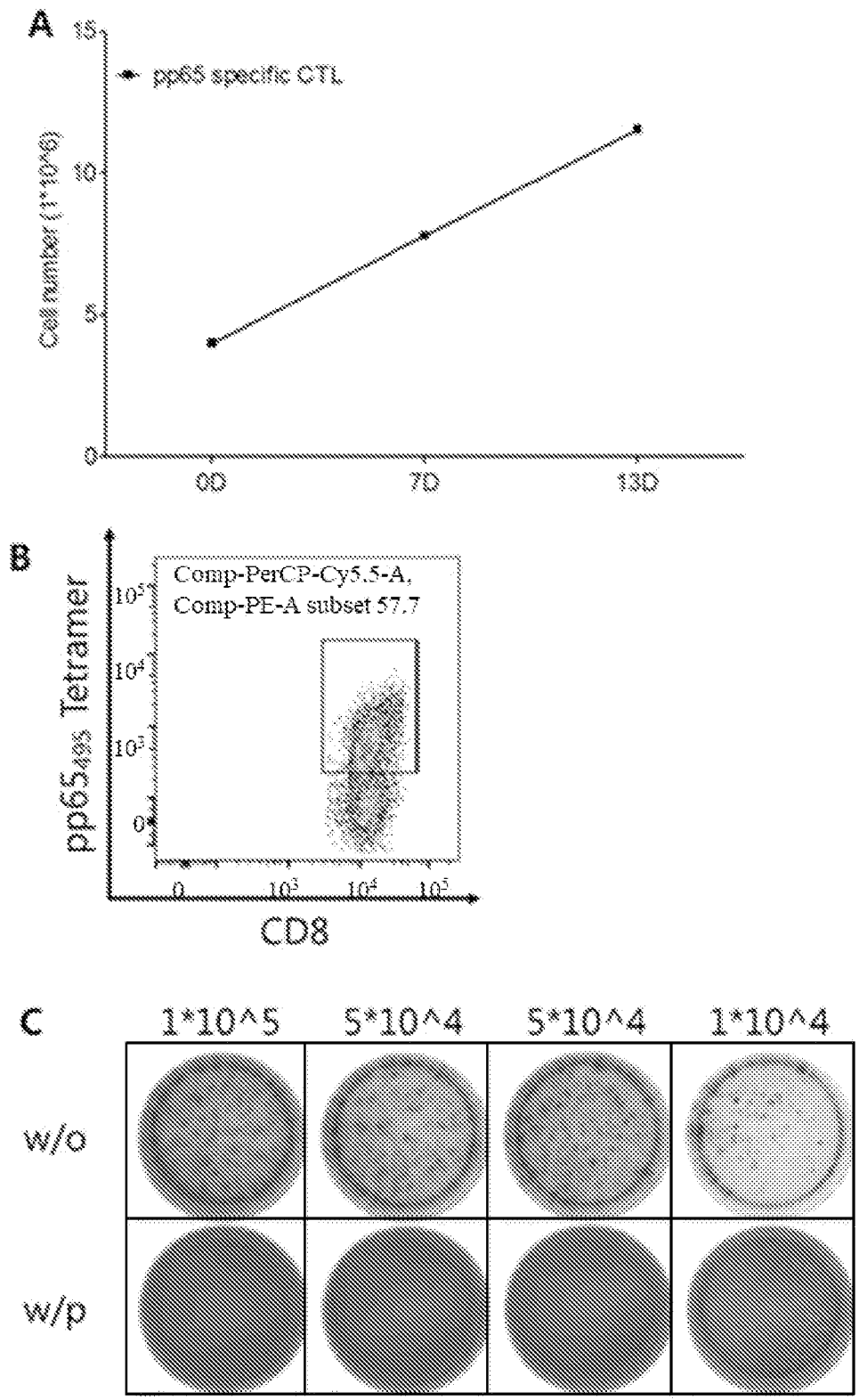
FIG. 7 illustrates a production result of pp65 specific cytotoxic T cells by 293T-Cos(+CD54 +CD70) stimulation (n=1), A inserted in FIG. 7 shows the proliferation of pp65 specific cytotoxic T cells on days 0, 7, and 13, B inserted in FIG. 7 shows a pp65$_{495}$ tetramer staining result in pp65 specific cytotoxic T cells on day 13, and C inserted in FIG. 7 shows a picture of an ELISPOT plate without peptide (w/o) or with peptide (w/p) wells with respect to $1 \times 10^4$, $5 \times 10^4$, and $1 \times 10^4$ pp65 specific cytotoxic T cells on day 13.

As illustrated in FIG. 7, on day 13, 2.89-fold cell proliferation was shown in pp65 specific cytotoxic T cells, and pp65$_{495}$ tetramer positive cells were 57.7% (FIGS. 7A and 7B). Furthermore, ELISPOT analysis results exhibited responses strong enough to be immeasurable under all the conditions of $1 \times 10^5$, $5 \times 10^4$, and $1 \times 10^4$ (FIG. 7C).

From the results, it can be seen that the null-293T(H1E-45) cell line-based artificial antigen presenting cell can stimulate CTLs, meaning that the null-293T(H1E) cell line can be utilized as a source of novel artificial antigen presenting cells.

The present invention may be applied to the field of treating tumors, pathogenic infections, or autoimmune diseases.

What is claimed is:

1. A method to make one or more antigen-presenting cells, comprising:
   a) eliminating HLA-A, HLA-B and HLA-C in one or more 293T cells using a CRISPR-Cas9 system to make one or more HLA-null 293T cells,
     wherein the CRISPR-Cas9 system comprises single guide RNAs(sgRNAs) targeting each of:
   HLA-A exon 2(SEQ ID NO: 1) and exon 3(SEQ ID NO: 2),
   HLA-B exon 2(SEQ ID NO: 3) and exon 3(SEQ ID NO: 4),
   HLA-C exon 2(SEQ ID NO: 5) and exon 3(SEQ ID NO: 6); and
   b) introducing a co-stimulatory molecule group into the one or more HLA-null 293T cells to make one or more antigen-presenting cells,
     wherein the co-stimulatory molecule is selected from the group consisting of: CD80; CD83; CD54; CD32; 4-1BBL; and CD70.

* * * * *